US012806478B2

(12) United States Patent
Merfeld

(10) Patent No.: US 12,806,478 B2
(45) Date of Patent: Nov. 24, 2026

(54) VESTIBULAR TRAINING DEVICES AND METHODS FOR IMPROVING VESTIBULAR FUNCTION AND BALANCE AND REDUCING FALL RISK

(71) Applicant: Ohio State Innovation Foundation, Columbus, OH (US)

(72) Inventor: Daniel Merfeld, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 190 days.

(21) Appl. No.: 18/721,043

(22) PCT Filed: Dec. 16, 2022

(86) PCT No.: PCT/US2022/081818

§ 371 (c)(1),
(2) Date: Jun. 17, 2024

(87) PCT Pub. No.: WO2023/115008

PCT Pub. Date: Jun. 22, 2023

(65) Prior Publication Data

US 2025/0058176 A1 Feb. 20, 2025

Related U.S. Application Data

(60) Provisional application No. 63/290,435, filed on Dec. 16, 2021.

(51) Int. Cl.
*A63B 26/00* (2006.01)
*A61B 5/00* (2006.01)
*A61B 5/11* (2006.01)

(52) U.S. Cl.
CPC .......... *A63B 26/003* (2013.01); *A61B 5/1121* (2013.01); *A61B 5/486* (2013.01)

(58) Field of Classification Search
CPC ... A61B 5/1117; A61B 5/1071; A61B 5/1121; A61B 5/1128; A61B 5/4023;
(Continued)

(56) References Cited

U.S. PATENT DOCUMENTS 7,933,654 B2 4/2011 Merfeld et al.
8,092,355 B2 1/2012 Mortimer et al.
(Continued)

FOREIGN PATENT DOCUMENTS

AU 2021106605 A4 * 11/2021 ............. A61B 5/112

OTHER PUBLICATIONS

International Searching Authority (ISA/US). International Search Report and Written Opinion. PCT Application No. PCT/US2022/081818. Issued on Mar. 10, 2023. 8 pages.
(Continued)

*Primary Examiner* — Megan Anderson
*Assistant Examiner* — Jonathan A Dicuia
(74) *Attorney, Agent, or Firm* — Meunier Carlin & Curfman LLC

(57) ABSTRACT

A vestibular training device for improving vestibular function and balance and reducing fall risk of a subject may include a motion platform configured to support the subject and execute discrete motions, one or more input devices configured to enable the subject to provide responses to the motions, one or more feedback devices configured to provide the subject with feedback indicative of whether the responses are correct or incorrect, and a controller configured to cause the motion platform to execute a first motion, receive, via the one or more input devices, a first response indicative of the subject's perception of the first motion, cause the one or more feedback devices to provide first feedback indicative of whether the first response is correct or incorrect, determine a second motion based at least in part
(Continued)

on the first response, and cause the motion platform to execute the second motion.

20 Claims, 15 Drawing Sheets

(58) Field of Classification Search
CPC ..... A61B 5/486; A63B 71/0622; A63B 22/18; A63B 23/0458; A63B 26/003
See application file for complete search history.

(56) References Cited

U.S. PATENT DOCUMENTS

| | | | | |
|---|---|---|---|---|
| 11,273,344 | B2 | 3/2022 | Zets et al. | |
| 2011/0312473 | A1* | 12/2011 | Chu | A63B 69/0053 482/54 |
| 2019/0015035 | A1* | 1/2019 | Merfeld | A61B 5/702 |
| 2019/0232113 | A1 | 8/2019 | Zets et al. | |
| 2021/0236903 | A1* | 8/2021 | Briel | A63B 71/0622 |
| 2022/0125336 | A1* | 4/2022 | Reed | A61B 5/112 |
| 2022/0386936 | A1* | 12/2022 | Waddington | A61B 5/4595 |

OTHER PUBLICATIONS

Agrawal Y, Bremova T, Kremmyda O, Strupp M & MacNeilage PR (2013). Clinical testing of otolith function: perceptual thresholds and myogenic potentials. J Assoc Res Otolaryngol 14, 905-915.
Agrawal Y, Carey JP, Della Santina CC, Schubert MC & Minor LB (2009). Disorders of balance and vestibular function in US adults: data from the National Health and Nutrition Examination Survey, 2001-2004. Arch Intern Med 169, 938-944.
Agrawal Y, Carey JP, Hoffman HJ, Sklare DA & Schubert MC (2011). The modified Romberg Balance Test: normative data in U.S. adults. Otol Neurotol 32, 1309-1311.
Agrawal Y, Pineault KG & Semenov YR (2018). Health-related quality of life and economic burden of vestibular loss in older adults: Burden of Vestibular Loss in Older Adults. Laryngoscope Investigative Otolaryngology 3, 8-15.
Amitay S, Moore DR, Molloy K & Halliday LF (2015). Feedback valence affects auditory perceptual learning independently of feedback probability. PLoS One 10, e0126412.
Ball K & Sekuler R (1982). A specific and enduring improvement in visual motion discrimination. Science 218, 697-698.
Bermudez Rey MC, Clark TK & Merfeld DM (2017). Balance Screening of Vestibular Function in Subjects Aged 4 Years and Older: A Living Laboratory Experience. Front Neurol 8, 631.
Bermudez Rey MC, Clark TK, Wang W, Leeder T, Bian Y & Merfeld DM (2016). Vestibular Perceptual Thresholds Increase above the Age of 40. Front Neurol; DOI: 10.3389/fneur.2016.00162.
Beylergil SB, Karmali F, Wang W, Bermudez Rey MC & Merfeld DM (2019). Vestibular roll tilt thresholds partially mediate age-related effects on balance. In Progress in Brain Research, pp. 249-267. Elsevier. Available at: https://linkinghub.elsevier.com/retrieve/pii/S0079612319300950 [Accessed Sep. 8, 2019].
Bliss TV & Collingridge GL (1993). A synaptic model of memory: long-term potentiation in the hippocampus. Nature 361, 31-39.
Chaudhuri SE & Merfeld DM (2013). Signal detection theory and vestibular perception: III. Estimating unbiased fit parameters for psychometric functions. Exp Brain Res 225, 133-146.
Crane BT (2012). Roll aftereffects: influence of tilt and inter-stimulus interval. Exp Brain Res 223, 89-98.
Crane BT (2016). Perception of combined translation and rotation in the horizontal plane in humans. J Neurophysiol 116, 1275-1285.
Dosher B & Lu Z-L (2017). Visual Perceptual Learning and Models. Annu Rev Vis Sci 3, 343-363.
Dosher BA & Lu Z-L (1999). Mechanisms of perceptual learning. Vision Research25.
Gauthier GM & Robinson DA (1975). Adaptation of the human vestibuloocular reflex to magnifying lenses. Brain Res 92, 331-335.
Goldberg JM, Wilson VJ, Cullen KE, Angelaki DE, Broussard DM, Buttner-Ennever J, Fukushima K & Minor LB (2012). The Vestibular System: A Sixth Sense. Oxford University Press. Available at: http://www.oxfordscholarship.com/view/10.1093/acprof:oso/9780195167085.001.0001/a cprof-9780195167085 [Accessed May 5, 2020].
Hall CD, Herdman SJ, Whitney SL, Cass SP, Clendaniel RA, Fife TD, Furman JM, Getchius TSD, Goebel JA, Shepard NT & Woodhouse SN (2016). Vestibular Rehabilitation for Peripheral Vestibular Hypofunction: An Evidence-Based Clinical Practice Guideline: From the American Physical Therapy Association Neurology Section. J Neurol Phys Ther 40, 124-155.
Hartmann M, Furrer S, Herzog MH, Merfeld DM & Mast FW (2013). Self-motion perception training: thresholds improve in the light but not in the dark. Exp Brain Res 226, 231-240.
Herdman SJ, Schubert MC, Das VE & Tusa RJ (2003). Recovery of Dynamic Visual Acuity in Unilateral Vestibular Hypofunction. Arch Otolaryngol Head Neck Surg 129, 819.
Herdman SJ, Schubert MC & Tusa RJ (2001). Role of Central Preprogramming in Dynamic Visual Acuity With Vestibular Loss. Arch Otolaryngol Head Neck Surg 127, 1205.
Herzog MH & Fahle M (1997). The role of feedback in learning a vernier discrimination task. Vision Res 37, 2133-2141.
Irvine DRF (2018). Auditory perceptual learning and changes in the conceptualization of auditory cortex. Hearing Research 366, 3-16.
Karmali F, Bermudez Rey MC, Clark TK, Wang W & Merfeld DM (2017). Multivariate Analyses of Balance Test Performance, Vestibular Thresholds, and Age. Front Neurol 8, 578.
Karmali F, Chaudhuri SE, Yi Y & Merfeld DM (2016). Determining thresholds using adaptive procedures and psychometric fits: evaluating efficiency using theory, simulations, and human experiments. Exp Brain Res 234, 773-789.
Kenward MG & Roger JH (1997). Small Sample Inference for Fixed Effects from Restricted Maximum Likelihood. Biometrics 53, 983.
King S, Benoit C, Bandealy N & Karmali F (2019a). Chapter 14—The influence of target distance on perceptual self-motion thresholds and the vestibulo-ocular reflex during interaural translation. In Progress in Brain Research, ed. Ramat S & Shaikh AG, Mathematical Modelling in Motor Neuroscience: State of the Art and Translation to the Clinic. Ocular Motor Plant and Gaze Stabilization Mechanisms, pp. 197-208. Elsevier. Available at: https://www.sciencedirect.com/science/article/pii/S007961231930113X [Accessed Oct. 22, 2021].
King S, Priesol AJ, Davidi SE, Merfeld DM, Ehtemam F & Lewis RF (2019b). Self-motion perception is sensitized in vestibular migraine: pathophysiologic and clinical implications. Sci Rep 9, 14323.
Klaus MP, Schone CG, Hartmann M, Merfeld Dm, S chubert MC & Mast FW (2020). Roll tilt self-motion direction discrimination training: First evidence for perceptual learning. Atten Percept Psychophys; DOI: 10.3758/s13414-019-01967-2.
Kobel MJ, Wagner AR & Merfeld DM (2021). Impact of Gravity on the Perception of Linear Motion. J Neurophysiol; DOI: 10.1152/jn.00274.2021.
Leek MR (2001). Adaptive procedures in psychophysical research. Perception & Psychophysics 63, 1279-1292.
Lim K, Karmali F, Nicoucar K & Merfeld DM (2017). Perceptual precision of passive body tilt is consistent with statistically optimal cue integration. Journal of Neurophysiology 117, 2037-2052.
Lim K, Karmali F, Nicoucar K & Merfeld DM (2017). Perceptual precision of passive body tilt is consistent with statistically optimal cue integration. Journal of Neurophysiology 117, 2037-2052.Lim K & Merfeld DM (2012). Signal detection theory and vestibular perception: II. Fitting perceptual thresholds as a function of frequency. Exp Brain Res 222, 303-320.
Liu J, Lu Z-L & Dosher BA (2010). Augmented Hebbian reweighting: Interactions between feedback and training accuracy in perceptual learning. Journal of Vision 10, 29-29.

(56) References Cited

OTHER PUBLICATIONS

Lu Z-L, Liu J & Dosher BA (2010). Modeling mechanisms of perceptual learning with augmented Hebbian re-weighting. Vision Research 50, 375-390.
MacNeilage PR, Banks MS, DeAngelis GC & Angelaki DE (2010). Vestibular Heading Discrimination and Sensitivity to Linear Acceleration in Head and World Coordinates. Journal of Neuroscience 30, 9084-9094.
Maurer C & Peterka RJ (2005). A New Interpretation of Spontaneous Sway Measures Based on a Simple Model of Human Postural Control. Journal of Neurophysiology 93, 189-200.
Merfeld DM (2005). Vestibular Perception and Action Employ Qualitatively Different Mechanisms. II. VOR and Perceptual Responses During Combined Tilt&Translation. Journal of Neurophysiology 94, 199-205.
Merfeld DM (2011). Signal detection theory and vestibular thresholds: I. Basic theory and practical considerations. Exp Brain Res 210, 389-405.
Merfeld DM, Park S, Gianna-Poulin C, Black FO & Wood S (2005). I. Vestibular perception and action employ qualitatively different mechanisms. I. Frequency response of VOR and perceptual responses during Translation and Tilt. Journal of Neurophysiology 94, 186-198.
Neuhauser HK, Radtke A, von Brevern M, Lezius F, Feldmann M & Lempert T (2008). Burden of dizziness and vertigo in the community. Arch Intern Med 168, 2118-2124.
Prieto TE, Myklebust JB, Hoffmann RG, Lovett EG & Myklebust BM (1996). Measures of postural steadiness: differences between healthy young and elderly adults. IEEE Trans Biomed Eng 43, 956-966.
Sathian K, Deshpande G & Stilla R (2013). Neural Changes with Tactile Learning Reflect Decision-Level Reweighting of Perceptual Readout. Journal of Neuroscience 33, 5387-5398.
Schubert MC, Della Santina CC & Shelhamer M (2008a). Incremental angular vestibulo-ocular reflex adaptation to active head rotation. Exp Brain Res 191, 435-446.
Schubert MC & Migliaccio AA (2019). New advances regarding adaptation of the vestibulo-ocular reflex. Journal of Neurophysiology 122, 644-658.
Schubert MC & Migliaccio AA (2019). New advances regarding adaptation of the vestibulo-ocular reflex. Journal of Neurophysiology 122, 644-658.Schubert MC, Migliaccio AA, Clendaniel RA, Allak A & Carey JP (2008b). Mechanism of Dynamic Visual Acuity Recovery With Vestibular Rehabilitation. Archives of Physical Medicine and Rehabilitation 89, 500-507.
Staab JP, Eckhardt-Henn A, Horii A, Jacob R, Strupp M, Brandt T & Bronstein A (2017). Diagnostic criteria for persistent postural-perceptual dizziness (PPPD): Consensus document of the committee for the Classification of Vestibular Disorders of the Barany Society. VES 27, 191-208.
Valko Y, Lewis RF, Priesol AJ & Merfeld DM (2012). Vestibular Labyrinth Contributions to Human Whole-Body Motion Discrimination. Journal of Neuroscience 32, 13537-13542.
Wagner AR, Kobel MJ & Merfeld DM (2021). Vestibular Noise as a Contributor to Postural Sway. Vestibular Oriented Research Meeting. Orlando, FL.
Watanabe T & Sasaki Y (2015). Perceptual Learning: Toward a Comprehensive Theory. Annu Rev Psychol 66, 197-221.

* cited by examiner

VESTIBULAR TRAINING DEVICES AND METHODS FOR IMPROVING VESTIBULAR FUNCTION AND BALANCE AND REDUCING FALL RISK

CROSS REFERENCE TO RELATED APPLICATIONS

This application is a U.S. National application filed under 35 U.S.C. § 371 of PCT/US2022/081818, filed Dec. 16, 2022, which claims the benefit of priority to U.S. Provisional Application No. 63/290,435, filed Dec. 16, 2021, each of which is hereby incorporated by reference in their entirety.

FIELD OF THE DISCLOSURE

The present disclosure relates generally to vestibular function and more particularly to vestibular training devices and methods for improving vestibular function and balance and reducing fall risk.

BACKGROUND OF THE DISCLOSURE

Perceptual learning has been studied at length in the visual, auditory, and tactile domains. Yet, few attempts have been made to experimentally improve vestibular (i.e., self-motion) perception. The vestibular system, consisting of three angular accelerometers (the semicircular canals) and two linear accelerometers (the otolith organs), sense motion of the head in six dimensions. Thus, nearly all human movements require the vestibular system to appropriately process motion stimuli to enable an appropriate response. The importance of vestibular perception can be highlighted by the burden of perceptual dysfunction, such as dizziness and vertigo, that accompanies vestibular disorders and aging. In addition, recent data suggests that the impaired perception of a roll tilt stimulus (i.e., rotation about an earth horizontal, naso-occipital axis), which is reliant on integration of canal and otolith cues, correlates with age-related balance impairment. Thus, investigating methods to improve vestibular perception has the potential to improve the manner by which common outcomes of vestibular dysfunction are treated.

Vestibular perception, while often referenced, can be considered broadly as the ability to perceive motion of the head in the absence of alternative extra-vestibular (e.g., visual) cues.

Although methods vary, a standard method for quantifying vestibular perception is the use of a two alternative forced choice direction recognition task. Briefly, subjects are moved (e.g., rotated, translated, tilted) and asked to report their perceived direction of motion (e.g., right/left, up/down). These data are then analyzed to determine the vestibular perceptual threshold (i.e., the smallest motion which can be accurately perceived), which represents the level at which the delivered stimulus is able to be reliably perceived despite the presence of noise in the system (e.g., sensory noise and/or decision-making noise). In standard practice, these binary response data are fit to a psychometric function to derive threshold estimates, which are equivalent to the standard deviation or spread of the psychometric curve, and quantifies the imprecision of the perceptual responses. Thus, when this approach is used to quantify vestibular self-motion perception, vestibular thresholds can be more precisely defined as a measure of noise in the vestibular sensory pathway. Therefore, the present disclosure posits that any improvements in perceptual thresholds after perceptual training manifest secondary to an enhancement of the strength of the vestibular self-motion signal, relative to the level of internal sensory noise (i.e., increasing the vestibular signal to noise ratio).

SUMMARY OF THE DISCLOSURE

The present disclosure provides vestibular training devices and methods for improving vestibular function and balance and reducing fall risk of a subject. In one aspect, a vestibular training device for improving vestibular function and balance and reducing fall risk of a subject is provided. The vestibular training device may include a motion platform configured to support the subject thereon and to execute a set of discrete motions, one or more input devices configured to enable the subject to provide responses to the motions executed by the motion platform, one or more feedback devices configured to provide the subject with feedback indicative of whether the responses are correct or incorrect, and a controller in communication with the motion platform, the one or more input devices, and the one or more feedback devices. The controller may be configured to cause the motion platform to execute a first motion, receive, via the one or more input devices, a first response indicative of the subject's perception of the first motion, cause the one or more feedback devices to provide first feedback indicative of whether the first response is correct or incorrect, determine a second motion based at least in part on the first response, and cause the motion platform to execute the second motion.

In some embodiments, the controller may be further configured to receive, via the one or more input devices, a second response indicative of the subject's perception of the second motion, cause the one or more feedback devices to provide second feedback indicative of whether the second response is correct or incorrect, determine a third motion based at least in part on the second response, and cause the motion platform to execute the third motion. In some embodiments, the controller may be further configured to receive, via the one or more input devices, a second response indicative of the subject's perception of the second motion, cause the one or more feedback devices to provide second feedback indicative of whether the second response is correct or incorrect, determine a plurality of additional motions based at least in part on the second response, cause the motion platform to execute the additional motions, receive, via the one or more input devices, a plurality of additional responses indicative of the subject's perception of the additional motions, cause the one or more feedback devices to provide a plurality of additional feedback indicative of whether the additional responses are correct or incorrect, and determine a threshold of the subject based at least in part on the first response, the second response, and at least part of the additional responses, wherein the threshold is a biomarker for a fall risk of the subject.

In some embodiments, the controller may be further configured to determine that one of the additional responses is indicative of a lapse by the subject, and determine the threshold of the subject based at least in part on the first response, the second response, and at least part of the additional responses, while excluding the one of the additional responses indicative of a lapse by the subject. In some embodiments, the controller may be further configured to use a standard delete-one jackknife procedure to identify the biggest outlier to determine that the one of the additional responses is indicative of a lapse by the subject. In some embodiments, the controller may be further configured to use a standard bootstrap method to estimate sample distribution in order to provide strict statistical criteria to identify outliers. In some embodiments, the controller may be further configured to determine confidence in order to improve accuracy and precision of the threshold. In some embodiments, the controller may be further configured to determine subsequent motions to be executed by the motion platform based at least in part on the confidence.

In some embodiments, the controller may be further configured to compare the fall risk of the subject to values from a previously quantified population. In some embodiments, the controller may be further configured to determine that the fall risk of the subject is acceptable when the threshold is below a predetermined percentile for young healthy adults, and determine that training of the subject is recommended when the threshold is above the predetermined percentile. In some embodiments, the predetermined percentile may be the $50^{th}$ percentile for young healthy adults. In some embodiments, the training may be perceptual training. In some embodiments, the perceptual training may include motions individually tailored to improve self-motion perception of the subject. In some embodiments, the perceptual training may include motions individually tailored to improve self-motion perception of the subject by lowering a self-motion perceptual threshold of the subject. In some embodiments, the perceptual training may include tilt motions individually tailored to improve self-motion perception of the subject by lowering a tilt self-motion perceptual threshold of the subject. In some embodiments, the perceptual training may include roll tilt motions individually tailored to lower a roll tilt perceptual threshold of the subject. In some embodiments, the perceptual training may include pitch tilt motions individually tailored to lower a pitch tilt perceptual threshold of the subject. In some embodiments, the perceptual training may include simultaneous and synchronous roll and pitch tilt motions individually tailored to lower a roll tilt perceptual threshold and a pitch tilt perceptual threshold of the subject.

In some embodiments, the controller may be further configured to cause the motion platform to execute each of the discrete motions having a single cycle of sinusoidal acceleration. In some embodiments, the set of discrete motions may include between 10 and 1000 discrete motions. In some embodiments, the set of discrete motions may include one or more translational motions. In some embodiments, the set of discrete motions may include one or more rotational motions. In some embodiments, the set of discrete motions may include one or more tilt motions. In some embodiments, the set of discrete motions may include one or more roll tilt motions. In some embodiments, the controller may be further configured to cause the motion platform to execute each of the one or more roll tilt motions for a duration between 0.5 seconds and 10 seconds. In some embodiments, the controller may be further configured to determine roll tilt perception of the subject. In some embodiments, the controller may be further configured to determine a roll tilt threshold of the subject. In some embodiments, the motion platform may be configured to support the subject thereon in a seated position. In some embodiments, the motion platform may be configured to support the subject thereon in a standing position. In some embodiments, the motion platform may be configured to support the subject thereon in a lying-down position.

In some embodiments, the discrete motions may be individually tailored for the subject to enhance training. In some embodiments, the discrete motions may be individually tailored for the subject based at least in part on a previously determined threshold for the subject. In some embodiments, the discrete motions may be individually tailored for the subject to be at or near the previously determined threshold for the subject. In some embodiments, the discrete motions may be individually tailored for the subject using a standard 2-down/1-up staircase. In some embodiments, the discrete motions may be individually tailored for the subject using a standard 3-down/1-up staircase. In some embodiments, the discrete motions may be individually tailored for the subject using a standard 4-down/1-up staircase. In some embodiments, the discrete motions may be individually tailored for the subject using a maximum likelihood method. In some embodiments, the discrete motions may be incrementally changed over the course of a training session. In some embodiments, the discrete motions may be changed using a standard 2-down/1-up staircase with asymmetrical step sizes. In some embodiments, the discrete motions may be changed using a standard 3-down/1-up staircase with asymmetrical step sizes. In some embodiments, the discrete motions may be changed using a standard 4-down/1-up staircase with asymmetrical step sizes.

In some embodiments, the one or more input devices may include one or more handheld devices configured to enable the subject to provide the responses to the motions executed by the motion platform. In some embodiments, the one or more handheld devices may include a plurality of buttons configured to enable the subject to provide different types of the responses to the motions executed by the motion platform. In some embodiments, the responses may be indicative of the subject's perception of direction of the motions executed by the motion platform. In some embodiments, the one or more feedback devices may be configured to provide the subject with auditory feedback indicative of whether the responses are correct or incorrect. In some embodiments, the one or more feedback devices may be configured to provide the subject with visual feedback indicative of whether the responses are correct or incorrect. In some embodiments, the vestibular training device also may include a blindfold configured to cover the subject's eyes during testing or training. In some embodiments, the vestibular training device also may include noise-cancelling headphones configured to emit white noise while the motion platform executes each of the discrete motions. In some embodiments, the vestibular training device also may include a visual display configured to present visual information during testing or training. In some embodiments, the vestibular training device also may include a visual display configured to present visual information immediately following each of the responses provided by the subject.

In another aspect, a method for improving vestibular function and balance and reducing fall risk of a subject using a vestibular training device is provided. The vestibular training device may include a motion platform configured to support the subject thereon and to execute a set of discrete motions, one or more input devices configured to enable the subject to provide responses to the motions executed by the motion platform, one or more feedback devices configured to provide the subject with feedback indicative of whether the responses are correct or incorrect, and a controller in communication with the motion platform, the one or more input devices, and the one or more feedback devices. The method may include causing the motion platform to execute a first motion, receiving, via the one or more input devices, a first response indicative of the subject's perception of the first motion, causing the one or more feedback devices to provide first feedback indicative of whether the first response is correct or incorrect, determining a second motion based at least in part on the first response, and causing the motion platform to execute the second motion.

In some embodiments, the method also may include receiving, via the one or more input devices, a second response indicative of the subject's perception of the second motion, causing the one or more feedback devices to provide second feedback indicative of whether the second response is correct or incorrect, determining a third motion based at least in part on the second response, and causing the motion platform to execute the third motion. In some embodiments, the method also may include receiving, via the one or more input devices, a second response indicative of the subject's perception of the second motion, causing the one or more feedback devices to provide second feedback indicative of whether the second response is correct or incorrect, determining a plurality of additional motions based at least in part on the second response, causing the motion platform to execute the additional motions, receiving, via the one or more input devices, a plurality of additional responses indicative of the subject's perception of the additional motions, causing the one or more feedback devices to provide a plurality of additional feedback indicative of whether the additional responses are correct or incorrect, and determining a threshold of the subject based at least in part on the first response, the second response, and at least part of the additional responses, wherein the threshold is a biomarker for a fall risk of the subject.

In some embodiments, the method also may include determining that one of the additional responses is indicative of a lapse by the subject, and determining the threshold of the subject based at least in part on the first response, the second response, and at least part of the additional responses, while excluding the one of the additional responses indicative of a lapse by the subject. In some embodiments, a standard delete-one jackknife procedure may be used to identify the biggest outlier to determine that the one of the additional responses is indicative of a lapse by the subject. In some embodiments, a standard bootstrap method may be used to estimate sample distribution in order to provide strict statistical criteria to identify outliers. In some embodiments, the method also may include determining confidence in order to improve accuracy and precision of the threshold. In some embodiments, the method also may include determining subsequent motions to be executed by the motion platform based at least in part on the confidence.

In some embodiments, the method also may include comparing the fall risk of the subject to values from a previously quantified population. In some embodiments, the method also may include determining that the fall risk of the subject is acceptable when the threshold is below a predetermined percentile for young healthy adults, and determining that training of the subject is recommended when the threshold is above the predetermined percentile. In some embodiments, the predetermined percentile is the $50^{th}$ percentile for young healthy adults. In some embodiments, the training is perceptual training. In some embodiments, the perceptual training may include motions individually tailored to improve self-motion perception of the subject. In some embodiments, the perceptual training may include motions individually tailored to improve self-motion perception of the subject by lowering a self-motion perceptual threshold of the subject. In some embodiments, the perceptual training may include tilt motions individually tailored to improve self-motion perception of the subject by lowering a tilt self-motion perceptual threshold of the subject. In some embodiments, the perceptual training may include roll tilt motions individually tailored to lower a roll tilt perceptual threshold of the subject. In some embodiments, the perceptual training may include pitch tilt motions individually tailored to lower a pitch tilt perceptual threshold of the subject. In some embodiments, the perceptual training may include simultaneous and synchronous roll and pitch tilt motions individually tailored to lower a roll tilt perceptual threshold and a pitch tilt perceptual threshold of the subject.

In some embodiments, the method also may include causing the motion platform to execute each of the discrete motions having a single cycle of sinusoidal acceleration. In some embodiments, the set of discrete motions may include between 10 and 1000 discrete motions. In some embodiments, the set of discrete motions may include one or more translational motions. In some embodiments, the set of discrete motions may include one or more rotational motions. In some embodiments, the set of discrete motions may include one or more tilt motions. In some embodiments, the set of discrete motions may include one or more roll tilt motions. In some embodiments, the method also may include causing the motion platform to execute each of the one or more roll tilt motions for a duration between 0.5 seconds and 10 seconds. In some embodiments, the method also may include determining roll tilt perception of the subject. In some embodiments, the method also may include determining a roll tilt threshold of the subject. In some embodiments, the subject may be supported on the motion platform in a seated position. In some embodiments, the subject may be supported on the motion platform in a standing position. In some embodiments, the subject may be supported on the motion platform in a lying-down position.

In some embodiments, the discrete motions may be individually tailored for the subject to enhance training. In some embodiments, the discrete motions may be individually tailored for the subject based at least in part on a previously determined threshold for the subject. In some embodiments, the discrete motions may be individually tailored for the subject to be at or near the previously determined threshold for the subject. In some embodiments, the discrete motions may be individually tailored for the subject using a standard 2-down/1-up staircase. In some embodiments, the discrete motions may be individually tailored for the subject using a standard 3-down/1-up staircase. In some embodiments, the discrete motions may be individually tailored for the subject using a standard 4-down/1-up staircase. In some embodiments, the discrete motions may be individually tailored for the subject using a maximum likelihood method. In some embodiments, the discrete motions may be incrementally changed over the course of a training session. In some embodiments, the discrete motions may be changed using a standard 2-down/1-up staircase with asymmetrical step sizes. In some embodiments, the discrete motions may be changed using a standard 3-down/1-up staircase with asymmetrical step sizes. In some embodiments, the discrete motions may be changed using a standard 4-down/1-up staircase with asymmetrical step sizes.

In some embodiments, the one or more input devices may include one or more handheld devices configured to enable the subject to provide the responses to the motions executed by the motion platform. In some embodiments, the one or more handheld devices may include a plurality of buttons configured to enable the subject to provide different types of the responses to the motions executed by the motion platform. In some embodiments, the responses may be indicative of the subject's perception of direction of the motions executed by the motion platform. In some embodiments, the one or more feedback devices may be configured to provide the subject with auditory feedback indicative of whether the responses are correct or incorrect. In some embodiments, the one or more feedback devices may be configured to provide the subject with visual feedback indicative of whether the responses are correct or incorrect. In some embodiments, the subject's eyes may be covered with a blindfold during testing. In some embodiments, the subject's eyes may be covered with a blindfold during training. In some embodiments, the method also may include emitting white noise, via noise-cancelling headphones positioned on the subject's ears, while the motion platform executes each of the discrete motions. In some embodiments, the method also may include presenting visual information to the subject, via a visual display, during testing. In some embodiments, the visual information may include virtual information. In some embodiments, the visual information may include real information. In some embodiments, the method also may include presenting visual information to the subject, via a visual display, during training. In some embodiments, the visual information may include virtual information. In some embodiments, the visual information may include real information. In some embodiments, the subject's eyes may be covered with a blindfold during each of the discrete motions executed by the motion platform, and the method also may include presenting visual information to the subject, via a visual display, immediately following each of the responses provided by the subject. In some embodiments, the method also may include presenting visual information to the subject during a second roll tilt motion, via a visual display that provides visual feedback throughout the duration of the roll tilt motion.

These and other aspects and improvements of the present disclosure will become apparent to one of ordinary skill in the art upon review of the following detailed description when taken in conjunction with the several drawings and the appended claims.

Figure 1:
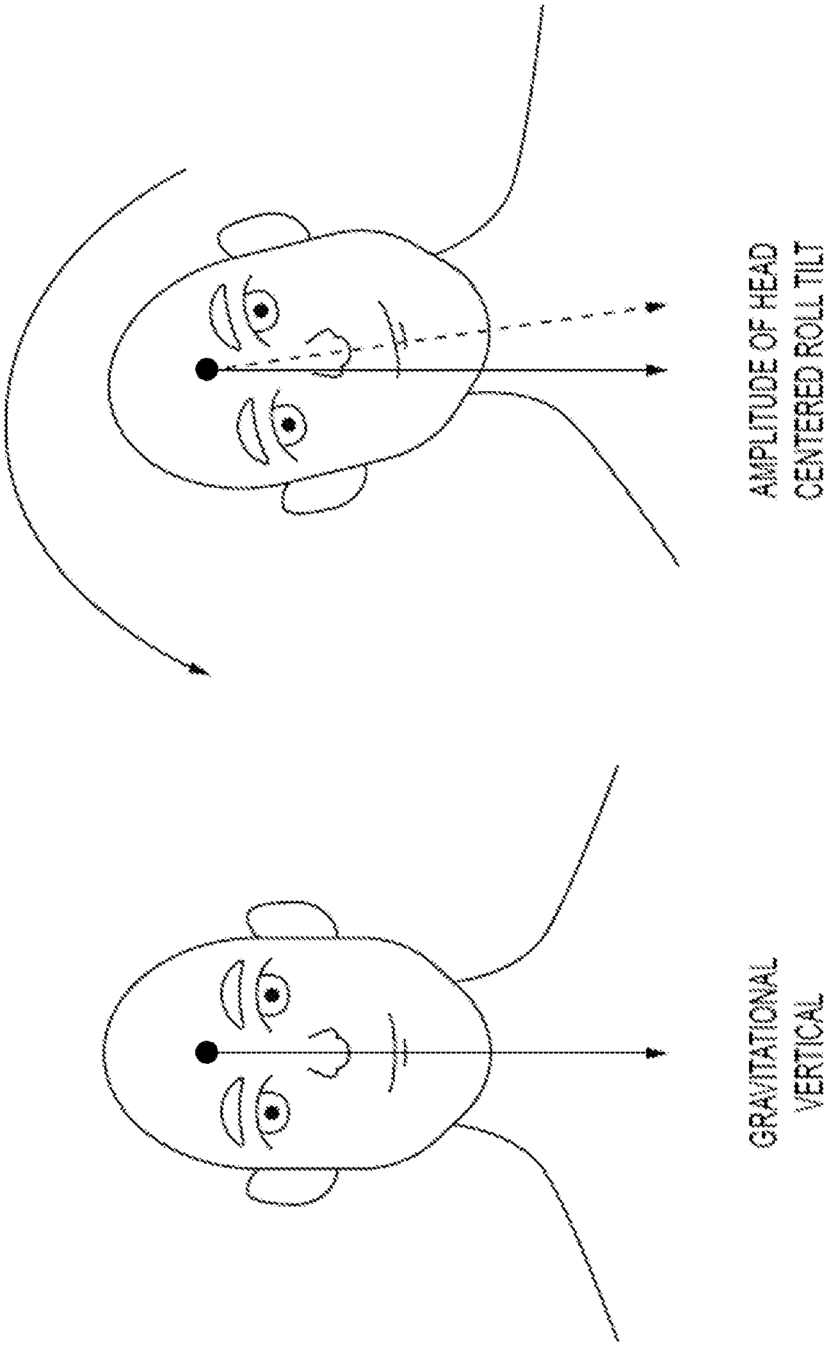
FIG. 1 illustrates a rightward head centered roll tilt motion. The amplitude of roll tilt reflects the angle between gravitational vertical (solid arrow) and the midline of the body (dashed arrow) at the conclusion of the motion. The axis is positioned midway between the labyrinths to provide an earth-horizontal rotation stimulus without concurrent lateral translation of the head.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION OF THE DISCLOSURE

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, and components have not been described in detail so as not to unnecessarily obscure aspects of the embodiments.

Overview

Roll tilt vestibular perceptual thresholds, an assay of vestibular noise, were recently found to correlate with quiet stance balance in a population of asymptomatic adults. It was subsequently hypothesized that roll tilt perceptual learning would yield improvements in both perceptual precision (i.e., vestibular thresholds), as well as quiet stance balance performance, consistent with vestibular imprecision being a cause of subclinical balance dysfunction. Data disclosed herein shows that in at least healthy young adults, roll tilt perceptual thresholds can be reduced by approximately twenty percent after less than 5 hours of training. Improvements in balance were modest, but significant reductions in quiet stance postural sway were observed in the conditions where ankle proprioceptive cues were degraded by standing on foam. These preliminary results will inform further development of roll tilt perceptual training as a means to improve self-motion perception and balance in older adults and in individuals with vestibular disorders.

As disclosed herein, roll tilt self-motion perception, as well as balance performance, can be improved through a vestibular perceptual learning intervention. Two intervention groups (N=10 each) performed 1300 trials of roll tilt at either 0.5 Hz (2 sec per motion) or 0.2 Hz (5 sec per motion) distributed over 5 days; each intervention group was provided feedback (correct/incorrect) after each trial. Roll tilt perceptual thresholds, measured using 0.2, 0.5 and 1 Hz stimuli, as well as quiet stance postural sway, were measured on day one and day six of the study. A control group (N=10) performed no perceptual training and showed stable 0.2 Hz (+1.5%, $p>0.999$), 0.5 Hz (−4.0%, $p>0.999$), and 1 Hz (−17.4%, $p=0.233$) thresholds. The 0.2 Hz training group demonstrated significant improvements in both 0.2 Hz (−23.8%, $p=0.009$) and 0.5 Hz (−22.2%, 0.047) roll tilt thresholds. The 0.5 Hz training group showed a significant improvement in 0.2 Hz thresholds (−19.1%, $p=0.047$), but not 0.5 Hz thresholds (−17.7%, $p=0.074$). Neither training group improved significantly at the untrained 1 Hz frequency ($p>0.05$). Although improvements in balance performance were less robust, the 0.5 Hz group showed significant decreases in sway in conditions of the Modified Romberg Balance Test where proprioceptive cues were degraded ["eyes open, on foam" ($p=0.032$) and "eyes closed, on foam" ($p<0.001$)]. These data suggest that roll tilt perception can be improved with less than 5 hours of training and that vestibular perceptual training may contribute to improvements in subclinical postural stability.

In one aspect, the present study measured changes in roll tilt thresholds using 0.2 and 0.5 Hz training stimuli in an independent sample of healthy adult volunteers. In addition, this study determined whether thresholds could be improved in nearly half the time (<5 hours) by using an adaptative (i.e., 2D/1U staircase that changes secondary to subject responses), rather than a fixed (training stimulus based only on baseline thresholds) roll tilt stimulus. Quiet stance balance was quantified before and after the roll tilt training protocol to determine whether, by reducing roll tilt vestibular noise (i.e., increasing precision of one's perception of the roll tilt stimulus), quiet stance postural sway would also decrease. As a result, this project not only provided insight into the potential of vestibular perceptual learning but also assessed whether roll tilt noise may be a cause, rather than only a correlate, of subclinical increases in postural sway.

Figure 7:
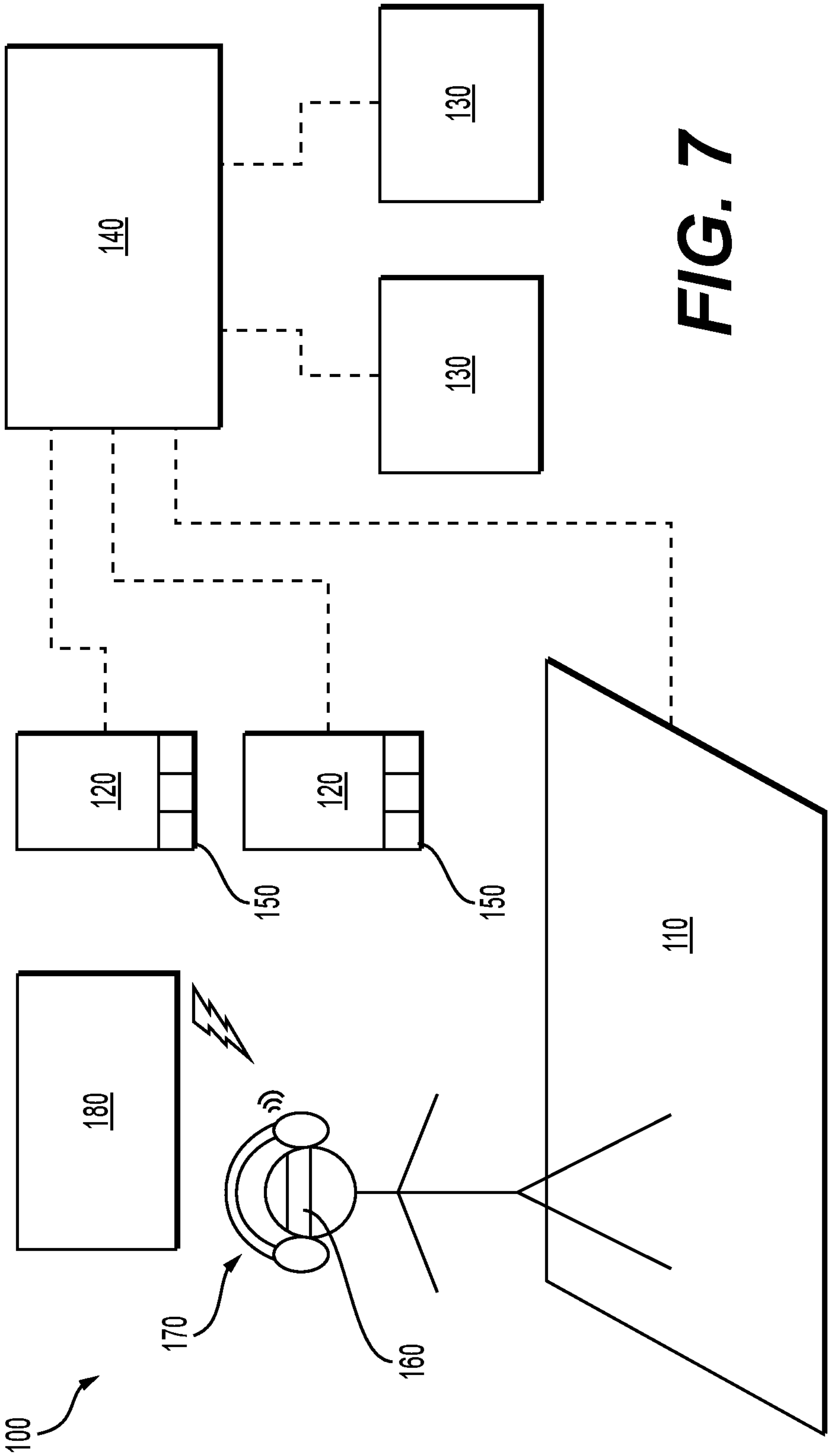
FIG. 7 shows a diagram of a vestibular training device for improving vestibular function and balance and reducing fall risk of a subject, according to one implementation.

The present disclosure provides vestibular training devices and methods for improving vestibular function and balance and reducing fall risk of a subject. In one aspect, a vestibular training device 100 for improving vestibular function and balance and reducing fall risk of a subject is provided, as shown in FIG. 7. The vestibular training device 100 may include a motion platform 110 configured to support the subject thereon and to execute a set of discrete motions, one or more input devices 120 configured to enable the subject to provide responses to the motions executed by the motion platform 110, one or more feedback devices 130 configured to provide the subject with feedback indicative of whether the responses are correct or incorrect, and a controller 140 in communication with the motion platform 110, the one or more input devices 120, and the one or more feedback devices 130. The controller 140 may be configured to cause the motion platform 110 to execute a first motion, receive, via the one or more input devices 120, a first response indicative of the subject's perception of the first motion, cause the one or more feedback devices 130 to provide a first feedback indicative of whether the first response is correct or incorrect, determine a second motion based at least in part on the first response, and cause the motion platform 110 to execute the second motion.

In some embodiments, the controller 140 may be further configured to receive, via the one or more input devices 120, a second response indicative of the subject's perception of the second motion, cause the one or more feedback devices 130 to provide a second feedback indicative of whether the second response is correct or incorrect, determine a third motion based at least in part on the second response, and cause the motion platform 110 to execute the third motion. In some embodiments, the controller 140 may be further configured to receive, via the one or more input devices 120, a second response indicative of the subject's perception of the second motion, cause the one or more feedback devices 130 to provide second feedback indicative of whether the second response is correct or incorrect, determine a plurality of additional motions based at least in part on the second response, cause the motion platform 110 to execute the additional motions, receive, via the one or more input devices 120, a plurality of additional responses indicative of the subject's perception of the additional motions, cause the one or more feedback devices 130 to provide a plurality of additional feedback indicative of whether the additional responses are correct or incorrect, and determine a threshold of the subject based at least in part on the first response, the second response, and at least part of the additional responses, wherein the threshold is a biomarker for a fall risk of the subject.

In some embodiments, the controller 140 may be further configured to determine that one of the additional responses is indicative of a lapse by the subject and determine the threshold of the subject based at least in part on the first response, the second response, and at least part of the additional responses, while excluding the one of the additional responses is indicative of a lapse by the subject. In some embodiments, the controller 140 may be further configured to use a standard delete-one jackknife procedure to identify the biggest outlier to determine that the one of the additional responses is indicative of a lapse by the subject. In some embodiments, the controller 140 may be further configured to use a standard bootstrap method to estimate sample distribution in order to provide strict statistical criteria to identify outliers. In some embodiments, the controller 140 may be further configured to determine confidence in order to improve accuracy and precision of the threshold. In some embodiments, the controller 140 may be further configured to determine subsequent motions to be executed by the motion platform 110 based at least in part on the confidence.

In some embodiments, the controller 140 may be further configured to compare the fall risk of the subject to values from a previously quantified population. In some embodiments, the controller 140 may be further configured to determine that the fall risk of the subject is acceptable when the threshold is below a predetermined percentile for young healthy adults, and determine that training of the subject is recommended when the threshold is above the predetermined percentile. In some embodiments, the predetermined percentile may be the $50^{th}$ percentile for young healthy adults. In some embodiments, the training may be perceptual training. In some embodiments, the perceptual training may include motions individually tailored to improve self-motion perception of the subject. In some embodiments, the perceptual training may include motions individually tailored to improve self-motion perception of the subject by lowering a self-motion perceptual threshold of the subject. In some embodiments, the perceptual training may include tilt motions individually tailored to improve self-motion perception of the subject by lowering a tilt self-motion perceptual threshold of the subject. In some embodiments, the perceptual training may include roll tilt motions individually tailored to lower a roll tilt perceptual threshold of the subject. In some embodiments, the perceptual training may include pitch tilt motions individually tailored to lower a pitch tilt perceptual threshold of the subject. In some embodiments, the perceptual training may include simultaneous and synchronous roll and pitch tilt motions individually tailored to lower a roll tilt perceptual threshold and a pitch tilt perceptual threshold of the subject.

In some embodiments, the controller 140 may be further configured to cause the motion platform 110 to execute each of the discrete motions having a single cycle of sinusoidal acceleration. In some embodiments, the set of discrete motions may include between 10 and 1000 discrete motions. In some embodiments, the set of discrete motions may include one or more translational motions. In some embodiments, the set of discrete motions may include one or more rotational motions. In some embodiments, the set of discrete motions may include one or more tilt motions. In some embodiments, the set of discrete motions may include one or more roll tilt motions. In some embodiments, the controller 140 may be further configured to cause the motion platform 110 to execute each of the one or more roll tilt motions for a duration between 0.5 seconds and 10 seconds. In some embodiments, the controller 140 may be further configured to determine roll tilt perception of the subject. In some embodiments, the controller 140 may be further configured to determine a roll tilt threshold of the subject. In some embodiments, the motion platform 110 may be configured to support the subject thereon in a seated position. In some embodiments, the motion platform 110 may be configured to support the subject thereon in a standing position. In some embodiments, the motion platform 110 may be configured to support the subject thereon in a lying-down position.

In some embodiments, the discrete motions may be individually tailored for the subject to enhance training. In some embodiments, the discrete motions may be individually tailored for the subject based at least in part on a previously determined threshold for the subject. In some embodiments, the discrete motions may be individually tailored for the subject to be at or near the previously determined threshold for the subject. In some embodiments, the discrete motions may be individually tailored for the subject using a standard 2-down/1-up staircase. In some embodiments, the discrete motions may be individually tailored for the subject using a standard 3-down/1-up staircase. In some embodiments, the discrete motions may be individually tailored for the subject using a standard 4-down/1-up staircase. In some embodiments, the discrete motions may be individually tailored for the subject using a maximum likelihood method. In some embodiments, the discrete motions may be incrementally changed over the course of a training session. In some embodiments, the discrete motions may be changed using a standard 2-down/1-up staircase with asymmetrical step sizes. In some embodiments, the discrete motions may be changed using a standard 3-down/1-up staircase with asymmetrical step sizes. In some embodiments, the discrete motions may be changed using a standard 4-down/1-up staircase with asymmetrical step sizes.

In some embodiments, the one or more input devices 120 may include one or more handheld devices configured to enable the subject to provide the responses to the motions executed by the motion platform 110. In some embodiments, the one or more handheld devices may include a plurality of buttons 150 configured to enable the subject to provide different types of the responses to the motions executed by the motion platform 110. In some embodiments, the responses may be indicative of the subject's perception of direction of the motions executed by the motion platform 110. In some embodiments, the one or more feedback devices 130 may be configured to provide the subject with auditory feedback indicative of whether the responses are correct or incorrect. In some embodiments, the one or more feedback devices 130 may be configured to provide the subject with visual feedback indicative of whether the responses are correct or incorrect. In some embodiments, the vestibular training device 100 also may include a blindfold 160 configured to cover the subject's eyes during testing or training. In some embodiments, the vestibular training device 100 also may include noise-cancelling headphones 170 configured to emit white noise while the motion platform 110 executes each of the discrete motions. In some embodiments, the vestibular training device 100 also may include a visual display 180 configured to present visual information during testing or training. In some embodiments, the vestibular training device 100 also may include a visual display 180 configured to present visual information immediately following each of the responses provided by the subject.

In another aspect, a method for improving vestibular function and balance and reducing fall risk of a subject using a vestibular training device 100 is provided. The vestibular training device 100 may include a motion platform 110 configured to support the subject thereon and to execute a set of discrete motions, one or more input devices 120 configured to enable the subject to provide responses to the motions executed by the motion platform 110, one or more feedback devices 130 configured to provide the subject with feedback indicative of whether the responses are correct or incorrect, and a controller 140 in communication with the motion platform 110, the one or more input devices 120, and the one or more feedback devices 130. The method may include causing the motion platform 110 to execute a first motion, receiving, via the one or more input devices 120, a first response indicative of the subject's perception of the first motion, causing the one or more feedback devices 130 to provide first feedback indicative of whether the first response is correct or incorrect, determining a second motion based at least in part on the first response, and causing the motion platform 110 to execute the second motion.

In some embodiments, the method also may include receiving, via the one or more input devices 120, a second response indicative of the subject's perception of the second motion, causing the one or more feedback devices 130 to provide second feedback indicative of whether the second response is correct or incorrect, determining a third motion based at least in part on the second response, and causing the motion platform 110 to execute the third motion. In some embodiments, the method also may include receiving, via the one or more input devices 120, a second response indicative of the subject's perception of the second motion, causing the one or more feedback devices 130 to provide second feedback indicative of whether the second response is correct or incorrect, determining a plurality of additional motions based at least in part on the second response, causing the motion platform 110 to execute the additional motions, receiving, via the one or more input devices 120, a plurality of additional responses indicative of the subject's perception of the additional motions, causing the one or more feedback devices 130 to provide a plurality of additional feedback indicative of whether the additional responses are correct or incorrect, and determining a threshold of the subject based at least in part on the first response, the second response, and at least part of the additional responses, wherein the threshold is a biomarker for a fall risk of the subject.

In some embodiments, the method also may include determining that one of the additional responses is indicative of a lapse by the subject and determining the threshold of the subject based at least in part on the first response, the second response, and at least part of the additional responses, while excluding the one of the additional responses is indicative of a lapse by the subject. In some embodiments, a standard delete-one jackknife procedure may be used to identify the biggest outlier to determine that the one of the additional responses is indicative of a lapse by the subject. In some embodiments, a standard bootstrap method may be used to estimate sample distribution in order to provide strict statistical criteria to identify outliers. In some embodiments, the method also may include determining confidence in order to improve accuracy and precision of the threshold. In some embodiments, the method also may include determining subsequent motions to be executed by the motion platform 110 based at least in part on the confidence.

In some embodiments, the method also may include comparing the fall risk of the subject to values from a previously quantified population. In some embodiments, the method also may include determining that the fall risk of the subject is acceptable when the threshold is below a predetermined percentile for young healthy adults and determining that training of the subject is recommended when the threshold is above the predetermined percentile. In some embodiments, the predetermined percentile is the $50^{th}$ percentile for young healthy adults. In some embodiments, the training is perceptual training. In some embodiments, the perceptual training may include motions individually tailored to improve self-motion perception of the subject. In some embodiments, the perceptual training may include motions individually tailored to improve self-motion perception of the subject by lowering a self-motion perceptual threshold of the subject. In some embodiments, the perceptual training may include tilt motions individually tailored to improve self-motion perception of the subject by lowering a tilt self-motion perceptual threshold of the subject. In some embodiments, the perceptual training may include roll tilt motions individually tailored to lower a roll tilt perceptual threshold of the subject. In some embodiments, the perceptual training may include pitch tilt motions individually tailored to lower a pitch tilt perceptual threshold of the subject. In some embodiments, the perceptual training may include simultaneous and synchronous roll and pitch tilt motions individually tailored to lower a roll tilt perceptual threshold and a pitch tilt perceptual threshold of the subject.

In some embodiments, the method also may include causing the motion platform 110 to execute each of the discrete motions having a single cycle of sinusoidal acceleration. In some embodiments, the set of discrete motions may include between 10 and 1000 discrete motions. In some embodiments, the set of discrete motions may include one or more translational motions. In some embodiments, the set of discrete motions may include one or more rotational motions. In some embodiments, the set of discrete motions may include one or more tilt motions. In some embodiments, the set of discrete motions may include one or more roll tilt motions. In some embodiments, the method also may include causing the motion platform 110 to execute each of the one or more roll tilt motions for a duration between 0.5 seconds and 10 seconds. In some embodiments, the method also may include determining roll tilt perception of the subject. In some embodiments, the method also may include determining a roll tilt threshold of the subject. In some embodiments, the subject may be supported on the motion platform 110 in a seated position. In some embodiments, the subject may be supported on the motion platform 110 in a standing position. In some embodiments, the subject may be supported on the motion platform 110 in a lying-down position.

In some embodiments, the discrete motions may be individually tailored for the subject to enhance training. In some embodiments, the discrete motions may be individually tailored for the subject based at least in part on a previously determined threshold for the subject. In some embodiments, the discrete motions may be individually tailored for the subject to be at or near the previously determined threshold for the subject. In some embodiments, the discrete motions may be individually tailored for the subject using a standard 2-down/1-up staircase. In some embodiments, the discrete motions may be individually tailored for the subject using a standard 3-down/1-up staircase. In some embodiments, the discrete motions may be individually tailored for the subject using a standard 4-down/1-up staircase. In some embodiments, the discrete motions may be individually tailored for the subject using a maximum likelihood method. In some embodiments, the discrete motions may be incrementally changed over the course of a training session. In some embodiments, the discrete motions may be changed using a standard 2-down/1-up staircase with asymmetrical step sizes. In some embodiments, the discrete motions may be changed using a standard 3-down/1-up staircase with asymmetrical step sizes. In some embodiments, the discrete motions may be changed using a standard 4-down/1-up staircase with asymmetrical step sizes.

In some embodiments, the one or more input devices 120 may include one or more handheld devices configured to enable the subject to provide the responses to the motions executed by the motion platform 110. In some embodiments, the one or more handheld devices may include a plurality of buttons 150 configured to enable the subject to provide different types of the responses to the motions executed by the motion platform 110. In some embodiments, the responses may be indicative of the subject's perception of direction of the motions executed by the motion platform 110. In some embodiments, the one or more feedback devices 130 may be configured to provide the subject with auditory feedback indicative of whether the responses are correct or incorrect. In some embodiments, the one or more feedback devices 130 may be configured to provide the subject with visual feedback indicative of whether the responses are correct or incorrect. In some embodiments, the subject's eyes may be covered with a blindfold 160 during testing. In some embodiments, the subject's eyes may be covered with a blindfold 160 during training. In some embodiments, the method also may include emitting white noise, via noise-cancelling headphones 170 positioned on the subject's ears, while the motion platform 110 executes each of the discrete motions. In some embodiments, the method also may include presenting visual information to the subject, via a visual display 180, during testing. In some embodiments, the visual information may include virtual information. In some embodiments, the visual information may include real information. In some embodiments, the method also may include presenting visual information to the subject, via a visual display 180, during training. In some embodiments, the visual information may include virtual information. In some embodiments, the visual information may include real information. In some embodiments, the subject's eyes may be covered with a blindfold 160 during each of the discrete motions executed by the motion platform 110, and the method also may include presenting visual information to the subject, via a visual display 180, immediately following each of the responses provided by the subject. In some embodiments, the method also may include presenting visual information to the subject during a second roll tilt motion, via a visual display 180 that provides visual feedback throughout the duration of the roll tilt motion.

It should be appreciated that the logical operations described herein with respect to the various figures may be implemented (1) as a sequence of computer implemented acts or program modules (i.e., software) running on a computing device (e.g., the computing device described in FIG. 8), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 8:
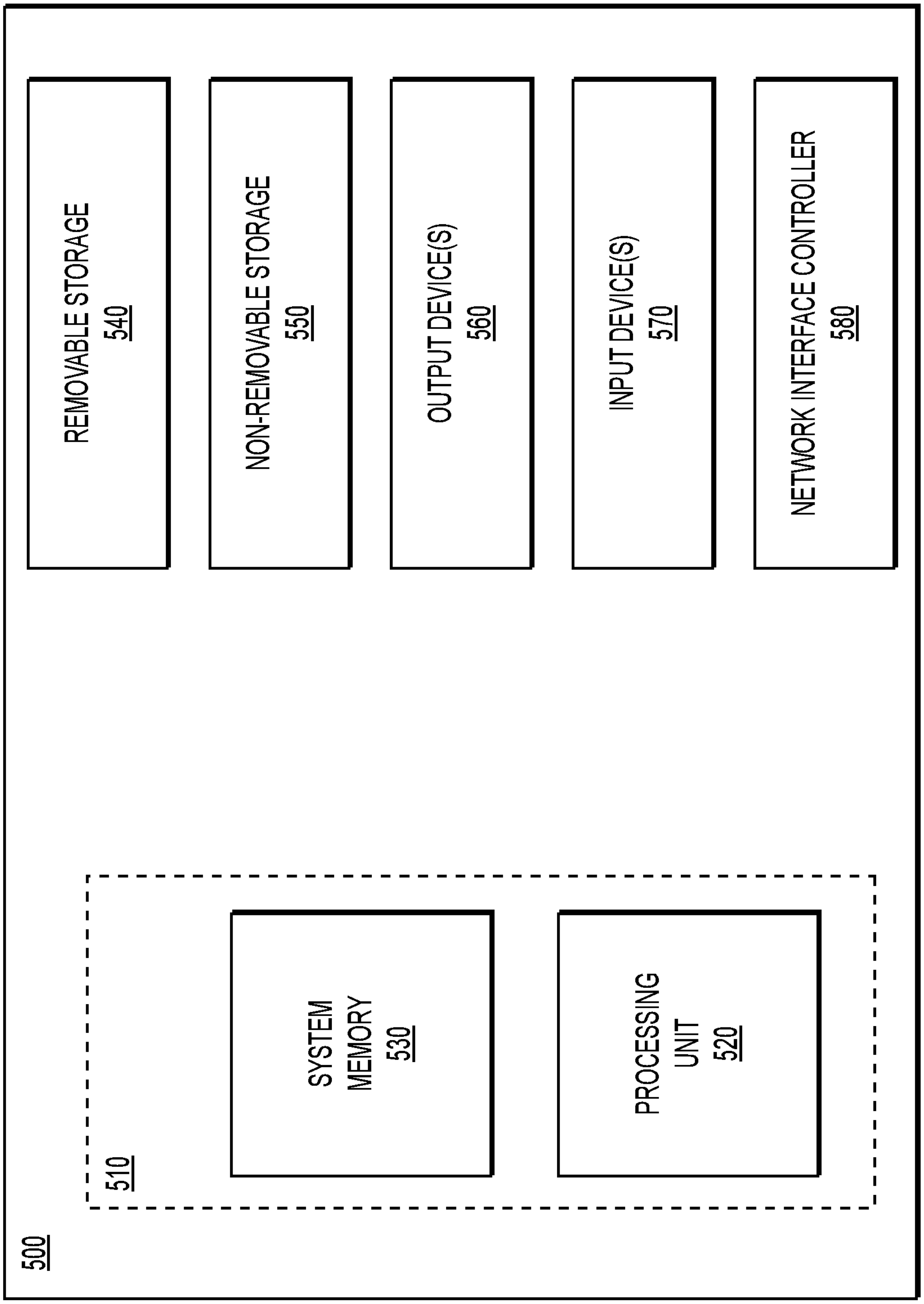
FIG. 8 shows an example computer system suitable for implementing the several embodiments of the disclosure.

Referring to FIG. 8, an example computing device 500 upon which embodiments of the invention may be implemented is illustrated. For example, the controller 140 described herein may each be implemented as a computing device, such as computing device 500. It should be understood that the example computing device 500 is only one example of a suitable computing environment upon which embodiments of the invention may be implemented. Optionally, the computing device 500 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In an embodiment, the computing device 500 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computing device 500 to provide the functionality of a number of servers that is not directly bound to the number of computers in the computing device 500. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In its most basic configuration, computing device 500 typically includes at least one processing unit 520 and system memory 530. Depending on the exact configuration and type of computing device, system memory 530 may be volatile (such as random access memory (RAM)), non-volatile (such as read-only memory (ROM), flash memory, etc.), or some combination of the two. This most basic configuration is illustrated in FIG. 8 by dashed line 510. The processing unit 520 may be a standard programmable processor that performs arithmetic and logic operations necessary for operation of the computing device 500. While only one processing unit 520 is shown, multiple processors may be present. Thus, while instructions may be discussed as executed by a processor, the instructions may be executed simultaneously, serially, or otherwise executed by one or multiple processors. The computing device 500 may also include a bus or other communication mechanism for communicating information among various components of the computing device 500.

Computing device 500 may have additional features/functionality. For example, computing device 500 may include additional storage such as removable storage 540 and non-removable storage 550 including, but not limited to, magnetic or optical disks or tapes. Computing device 500 may also contain network connection(s) 580 that allow the device to communicate with other devices such as over the communication pathways described herein. The network connection(s) 580 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. Computing device 500 may also have input device(s) 570 such as a keyboards, keypads, switches, dials, mice, track balls, touch screens, voice recognizers, card readers, paper tape readers, or other well-known input devices. Output device(s) 560 such as a printers, video monitors, liquid crystal displays (LCDs), touch screen displays, displays, speakers, etc. may also be included. The additional devices may be connected to the bus in order to facilitate communication of data among the components of the computing device 500. All these devices are well known in the art and need not be discussed at length here.

The processing unit 520 may be configured to execute program code encoded in tangible, computer-readable media. Tangible, computer-readable media refers to any media that is capable of providing data that causes the computing device 500 (i.e., a machine) to operate in a particular fashion. Various computer-readable media may be utilized to provide instructions to the processing unit 520 for execution. Example tangible, computer-readable media may include, but is not limited to, volatile media, non-volatile media, removable media and non-removable media implemented in any method or technology for storage of information such as computer readable instructions, data structures, program modules or other data. System memory 530, removable storage 540, and non-removable storage 550 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

In an example implementation, the processing unit 520 may execute program code stored in the system memory 530. For example, the bus may carry data to the system memory 530, from which the processing unit 520 receives and executes instructions. The data received by the system memory 530 may optionally be stored on the removable storage 540 or the non-removable storage 550 before or after execution by the processing unit 520.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Embodiments of the methods and systems may be described herein with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Methods

Thirty subjects were originally enrolled and began the study. Of the twenty subjects enrolled in the experimental arm, each was randomized into either the 0.2 or 0.5 Hz training group. The treatment intervention lasted 6 consecutive days and the control testing lasted 2 non-consecutive days. Total enrollment was 32, with 30 subjects completing the study (22 female). All participants reported no history of vestibular or neurologic disorder, or recent orthopedic injury. Both postural sway and vestibular thresholds increase beyond approximately age 40, and thus the recruited subjects' age ranged between 20 and 32 (Mean 25±3.55) to minimize potential confounding contributions of aging.

Vestibular Perceptual Thresholds

Vestibular perceptual thresholds were measured using a forced-choice direction recognition task, the most reliable way to assay sensory noise in humans. These methods have been used extensively when quantifying self-motion perceptual thresholds. The motion stimuli were delivered using a MOOG six degree of freedom motion platform and all testing took place in a dark, light tight room. Subjects were seated in a chair positioned atop the motion platform and were secured with a 5-point harness with the head restrained in a helmet mounted to the motion platform. To mask directional auditory cues, external noise was attenuated through use of insert headphones (~20 dB SPL) and white noise (~60 dB SPL) which was presented during each of the trial motions. The white noise started at the onset of the trial and terminated at the end, and as a result, provided an indication of the onset of the stimulus and a cue for the subject to provide a response.

Motion stimuli consisted of single cycles of sinusoidal acceleration [$(a(t)=A\ \sin(2\pi\ ft)$; A=peak acceleration, f=frequency, t=time) with frequency reflecting the inverse of the cycle duration (i.e., 1 Hz=1 second of motion). Peak velocity ($v_{peak}=AT/\pi$) and peak displacement ($D=AT^2/2\pi$) are proportional to the peak acceleration (A) (T=cycle duration, p=displacement). This stimulus is without position, velocity, or acceleration discontinuities and mimics typical head motion stimuli during natural motions. Thresholds were assessed at 0.2 Hz, 0.5 Hz and 1 Hz (i.e., stimuli lasting 5, 2, and 1 second, respectively). 0.2 and 0.5 Hz roll tilt thresholds rely on the integration of concomitant vertical semicircular canal and otolith (predominantly utricle) stimulation, whereas 1 Hz thresholds primarily reflect the precision of the vertical canal signal.

For each threshold assessment, subjects were tilted about a head-centered naso-occipital axis, such that the rotational axis was located midway between the vestibular labyrinths (FIG. 1). Once tilted, the participant was asked to report the direction of tilt using handheld buttons, and then was immediately returned to upright. To mitigate motion aftereffects a three second interval was provided between each test motion after the return to upright was complete. A symmetric 4D/1U staircase, in which peak velocity was decreased after four consecutive correct responses and increased after one incorrect response, was used to present stimuli that approach the estimated threshold value; simulations show that the use of a 4D1U staircase for the selection of test stimuli provides a balance between efficiency and precision. Stimulus step size was selected using parameter estimation by sequential testing (PEST) rules. One-hundred motions were completed for each test; while a larger number of trials would yield a more precise estimate of thresholds, prior simulations found only marginal improvements in the precision of threshold estimates when increasing the number of trials above 100.

The threshold parameter was ultimately determined by fitting the binary responses (e.g., left/right) and stimulus magnitudes (e.g., size and direction of the roll tilt stimulus) to a Gaussian cumulative distribution function. A bias reduced generalized linear model (Matlab brglmfit) with a probit link function was used to minimize the expected underestimation of thresholds introduced by the use of an adaptive sampling scheme. The psychometric function is defined by both the standard deviation, which is the threshold parameter, and mean, which represents the vestibular bias and the offset of the psychometric function along the abscissa from zero. The threshold parameter, given its direct association with vestibular noise, serves as a primary parameter of interest in this study.

Postural Control

Postural control was quantified using a triaxial force plate (AMTI Accusway) to record the displacement of the center of pressure (CoP) under various quiet stance conditions. These conditions included the standard conditions of the Romberg Test of Standing Balance on Firm and Compliant Support Surfaces with the addition of two conditions (eyes open/closed) assessing tandem stance (heel-to-toe) while on foam (Table 1). Subjects stood with the arms folded and feet in narrow (or tandem) stance for 30 (conditions 1,3,5,6) or 60 (conditions 2,4) seconds. The difference in durations reflects an emphasis on vestibular function, which increases in conditions of eyes closed stance. Thus, the period of testing for such conditions was extended. The primary measure of interest was the root mean square distance (RMSD) of the CoP in the mediolateral plane. The RMSD represents the average magnitude by which the CoP deviates when attempting to maintain a quiet stance; this is effectively the standard deviation of the zero-meaned CoP tracing. For the "vestibular" condition (i.e., condition 4), where subjects stood with eyes closed on a foam surface changes in the mean velocity and mean frequency of the mediolateral CoP were also quantified, as these metrics reflect different aspects of postural control independent from the RMSD.

TABLE 1

Balance test conditions. Participants stood with feet together and arms folded across the chest for conditions 1 through 4; for tandem stance conditions, participants stood heel-to-toe with the dominant foot in front.

| Test Condition | Description | Duration | Sensory Inputs |
| --- | --- | --- | --- |
| 1 | Eyes open, firm surface | 30 | Visual, proprioceptive, vestibular |
| 2 | Eyes closed, firm surface | 60 | Proprioceptive, vestibular |

TABLE 1-continued

Balance test conditions. Participants stood with feet together and arms folded across the chest for conditions 1 through 4; for tandem stance conditions, participants stood heel-to-toe with the dominant foot in front.

| Test Condition | Description | Duration | Sensory Inputs |
|---|---|---|---|
| 3 | Eyes open, compliant surface | 30 | Visual, vestibular |
| 4 | Eyes closed, compliant surface | 60 | Vestibular |
| 5 | Eyes open, compliant surface, tandem stance | 30 | Visual, vestibular |
| 6 | Eyes closed, compliant surface, tandem stance | 30 | Vestibular |

Roll Tilt Perceptual Training

The experimental groups performed 1300 trials of roll tilt training over a period of 5 days. The sole difference between the two experimental groups was in the frequency of the training stimulus (0.5 Hz vs. 0.2 Hz). Training was not assessed at 1 Hz (or higher frequencies), as these responses are dominated by canal cues and past evidence suggests learning may be specific for more complex motions which stimulate both the canals and otoliths. The control group only underwent baseline and post-test assessments of thresholds and balance. In contrast to the threshold test conditions, during training the participants were given feedback after each response to indicate whether they were correct or incorrect in their judgement of the motion direction. Feedback was given by unique auditory cues (i.e., a "chime" for correct, and a "buzzer" for incorrect) which were explicitly explained to all training participants before the training protocol. Also, a 2D1U, rather than 4D1U, staircase was used to target a stimulus level that would lead to an accuracy level of 70.1%. This was done to approximate the level of challenge (65% correct) shown previously to induce roll tilt perceptual learning.

The initial stimulus magnitude for the adaptive staircase for each training block (i.e., 100 trials) was modified on the basis of the participant's previous performance and selected to be 2× the threshold of the previous 100 trial run. In the paradigm used in previous studies the stimulus amplitude was selected based upon an individual's baseline threshold and held constant; as a result, improvements in roll tilt perception (i.e., lowering thresholds) during the training protocol would be expected to yield a training stimulus that targets a higher level of accuracy or a lesser amount of challenge. For example, a baseline threshold of 1°/s would warrant a training stimulus of 0.38°/s, however, if thresholds were to reduce to 0.5°/s with training, a 0.38°/s stimulus would be expected to yield an accuracy level of 78%. The adaptative 2D1U staircase was selected to instead maintain a consistent level of challenge (i.e., level of accuracy of perceptual judgments) despite the anticipated improvements in performance over the course of training. This staircase approach also forgives inaccuracies (e.g., inherent variability) in pre-training threshold measures. While the experimenter could not be blinded to group assignment in order to administer the correct training stimulus, the threshold protocols and training intervention described above are carried out using custom automated software and thus, are not reliant upon human input, aside from monitoring the testing session; also, perceptual threshold and CoP metrics were computed using automated Matlab programs.

Statistical Analysis

Linear mixed effect models (mixed; Stata v17.0, College Station, TX) were fit to the data to account for the repeated measured design. The main effects of time (baseline, post-test) and group (control, 0.5, 0.2 Hz) were included, as well as their interaction (group by time). Post-hoc comparisons were completed using tests of simple effects (i.e., partial F-tests); multiple comparisons were controlled for by computing Bonferroni corrected p-values. Separate mixed effect models were used for each of three frequencies of baseline thresholds (0.2, 0.5, and 1 Hz), as well as for each balance condition. The degrees of freedom in the mixed effect model were adjusted using the Kroger method to mitigate the increase in Type I error that results from the small sample size and the variability in estimates of the subject specific random effect term. To determine whether the extent of threshold improvement was associated with improvements in balance, the spearman rank correlation was calculated between the change in thresholds and the change in balance performance. Finally, to determine the proportion of subjects in each group who showed a meaningful improvement in thresholds after the intervention, the subjects were also categorized as "responders" or "non-responders." Simulations have shown that thresholds measured using a 4D1U staircase yield a variability of ~16% (1 SD); a meaningful change was defined as a reduction in thresholds of at least 2 SD (here defined as >32%) from the threshold value measured at baseline. Multivariate logistic regression was used to determine whether the odds of responding favorably to the intervention was affected by age, baseline thresholds, or sex.

Results

Baseline Comparison of Groups

Univariate linear regression models were used to compare the threshold measures (0.2, 0.5, and 1 Hz) and postural sway metrics between each of the three groups at baseline. The 0.5 Hz training group showed significantly higher RMSD in the "eyes open, on foam condition" compared to the control group (p=0.004), otherwise no significant differences were observed between any of the groups for any of the chosen metrics (p>0.05; Table 2).

TABLE 2

Baseline mean (SD) data is shown and p-values reflect the effect of Group in separate linear mixed effect models.

| | Control | 0.2 Hz | 0.5 Hz | p-value |
|---|---|---|---|---|
| No. of Subjects (Female) | 10 (8) | 10 (7) | 10 (4) | N/A |
| Age (years) | 26.8 (3.33) Range: 21-32 | 23.6 (3.27) Range: 21-31 | 24.7 (3.59) Range: 20-31 | 0.165 |
| 0.2 Hz Roll Tilt (°/s) | 0.44 (0.19) | 0.46 (0.21) | 0.58 (0.24) | 0.155 |
| 0.5 Hz Roll Tilt (°/s) | 0.73 (0.35) | 0.75 (0.32) | 0.75 (0.34) | 0.900 |
| 1 Hz Roll Tilt (°/s) | 0.83 (0.34) | 0.86 (0.35) | 0.981 (0.38) | 0.330 |
| EO/Firm (mm): RMSD | 3.98 (0.96) | 4.20 (1.30) | 4.48 (1.92) | 0.416 |
| EC/Firm (mm): RMSD | 5.46 (1.16) | 5.47 (1.53) | 6.28 (1.63) | 0.188 |
| EO/Foam (mm): RMSD | 5.74 (1.76) | 6.72 (2.53) | 8.82 (3.01) | 0.004* |
| EC/Foam (mm): RMSD | 11.92 (3.58) | 11.16 (3.32) | 12.60 (2.81) | 0.626 |
| EO/Foam/ Tandem (mm): RMSD | 5.94 (2.13) | 6.78 (2.35) | 6.54 (3.80) | 0.623 |
| EC/Foam (mm/s): MVEL | 34.50 (10.31) | 33.48 (9.48) | 33.34 (8.34) | 0.472 |

TABLE 2-continued

Baseline mean (SD) data is shown and p-values reflect the effect of Group in separate linear mixed effect models.

| | Control | 0.2 Hz | 0.5 Hz | p-value |
|---|---|---|---|---|
| EC/Foam (Hz): MFREQ | 0.59 (0.10) | 0.63 (0.15) | 0.55 (0.14) | 0.772 |

RMS = root mean square displacement,
MVEL = mean velocity,
MFREQ = mean frequency,
EO = eyes open,
EC = eyes closed.
*= significant at $p < 0.05$.

Effect of Training on Roll Tilt Thresholds

Figure 2:
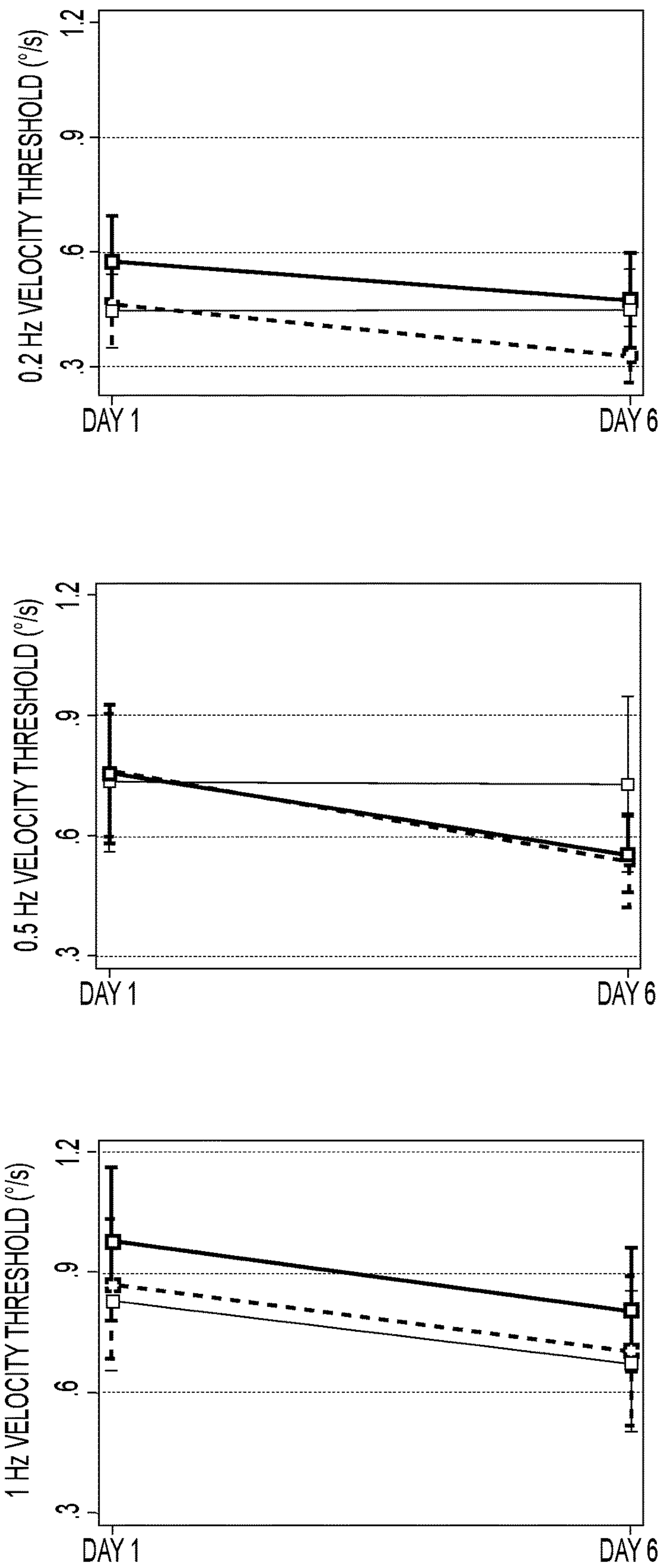
FIG. 2 illustrates mean roll tilt velocity thresholds for three groups of an example study (black—control, orange—0.2 Hz training group, green—0.5 Hz training group), as measured on Day 1 and Day 6. The 0.2 Hz and 0.5 Hz training groups completed a perceptual training protocol (using 0.2 Hz and 0.5 Hz stimuli, respectively) between threshold measurements, while the control group did not. Error bars represent 1 SD.

The control group showed consistent 0.2 Hz thresholds on days 1 and 6 of the study, on average increasing thresholds by 1.5% (p>0.999). The 0.2 Hz training group demonstrated a significant change in 0.2 Hz thresholds (p=0.009) improving an average of 23.8%, as did the 0.5 Hz training group (p=0.046) who improved an average of 19.1% (Table 3; FIG. 2). Group assignment modified the effect of time, such that the effect of time was greater for the 0.2 Hz group, compared to the control group (p=0.025). While approaching significance, the effect of time was not significantly different between the 0.5 Hz group and controls (p=0.069).

TABLE 3

Baseline (day 1) and post-test (day 6) thresholds are reported for each group. Average change in thresholds is reported. Bonferroni corrected 95% CI reflects the results of the post-hoc partial F-test comparing the effect of time (day 1 vs. day 6) for each group.

| | Day 1 | Day 6 | % Change | 95% CI |
|---|---|---|---|---|
| Control | | | | |
| 0.2 Hz Roll Tilt | 0.44(0.19) | 0.45(0.21) | 1.5 | −0.1 to 0.1 |
| 0.5 Hz Roll Tilt | 0.73(0.35) | 0.73(0.44) | 4.0 | −0.22 to 0.21 |
| 1.0 Hz Roll Tilt | 0.83(0.34) | 0.68(0.35) | 17.4 | −0.36 to 0.06 |
| 0.2 Hz Training | | | | |
| 0.2 Hz Roll Tilt | 0.46(0.21) | 0.33(0.15) | 23.8* | −0.23 to −0.028 |
| 0.5 Hz Roll Tilt | 0.75(0.32) | 0.54(0.24) | 22.2* | −0.43 to −0.002 |
| 1.0 Hz Roll Tilt | 0.86(0.35) | 0.70(0.37) | 17.8 | −0.37 to 0.05 |
| 0.5 Hz Training | | | | |
| 0.2 Hz Roll Tilt | 0.58(0.24) | 0.47(0.25) | 19.1 | −0.2 to −0.001 |
| 0.5 Hz Roll Tilt | 0.75(0.34) | 0.55(0.19) | 17.7 | −0.41 to 0.014 |
| 1.0 Hz Roll Tilt | 0.98(0.38) | 0.81(0.31) | 4.8 | −0.38 to 0.04 |

For 0.5 Hz roll tilt thresholds, the control group again showed minimal change in thresholds between days 1 and 6 (p>0.999, average decrease of 4%). A significant decrease in thresholds was observed for the 0.2 Hz group (p=0.046), but not for the 0.5 Hz group (p=0.074), after correcting for multiple comparisons. The 0.2 Hz group showed an average change of 22.2% compared to 17.7% for the 0.5 Hz group (Table 3; FIG. 2). In contrast to the significant interaction seen for 0.2 Hz thresholds, no significant group by time interactions were observed, suggesting that group assignment did not modify the effect of time on 0.5 Hz thresholds, putatively as a result of the variability in the response to treatment within the intervention groups (see below).

For 1 Hz roll tilt thresholds, similar improvements in thresholds were observed for each of the three groups, including the control group, this finding is consistent with previous studies. However, despite a decrease in mean thresholds at day 6 for each group (control=17.4%, 0.2 Hz=17.8%, 0.5 Hz=14.8%), the effect of time was not significant for any of the groups (p>0.05) and no group by time interaction effects were present (p>0.05) (Table 3; FIG. 2).

Classifying Treatment Responders

Figure 3A:
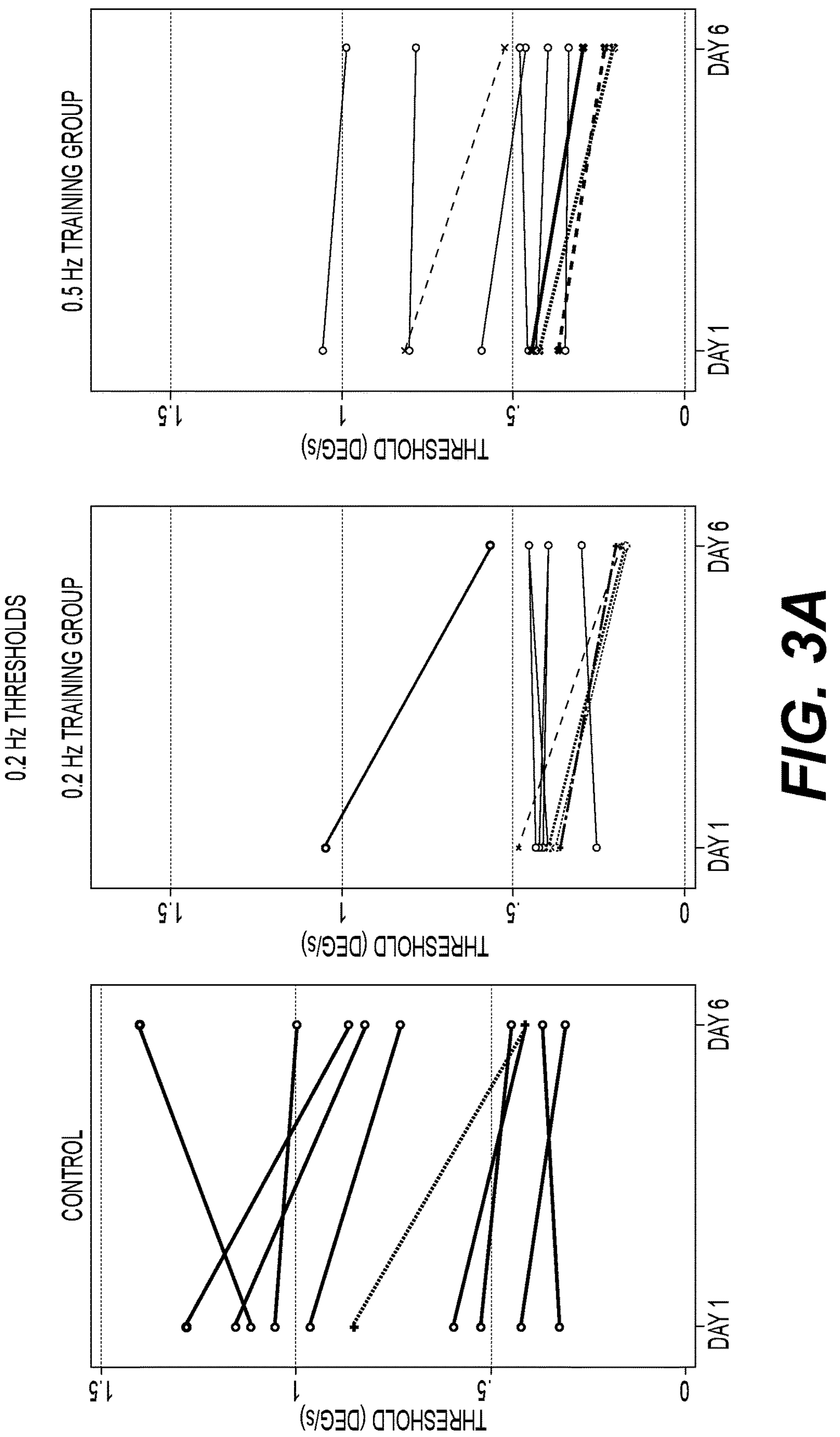
FIGS. 3A-3C illustrate vestibular thresholds for each individual on Day 1 and Day 6 for 0.2 Hz (A) 0.5 Hz (B) and 1 Hz (C) thresholds. Participants who were "responders" for the specific threshold measured (i.e., improved by at least 32%) are uniquely color coded in each panel, while the "non-responders" are depicted in black. Unique color codes are continued for individual subjects in FIGS. 5A-5E.
Figure 3B:
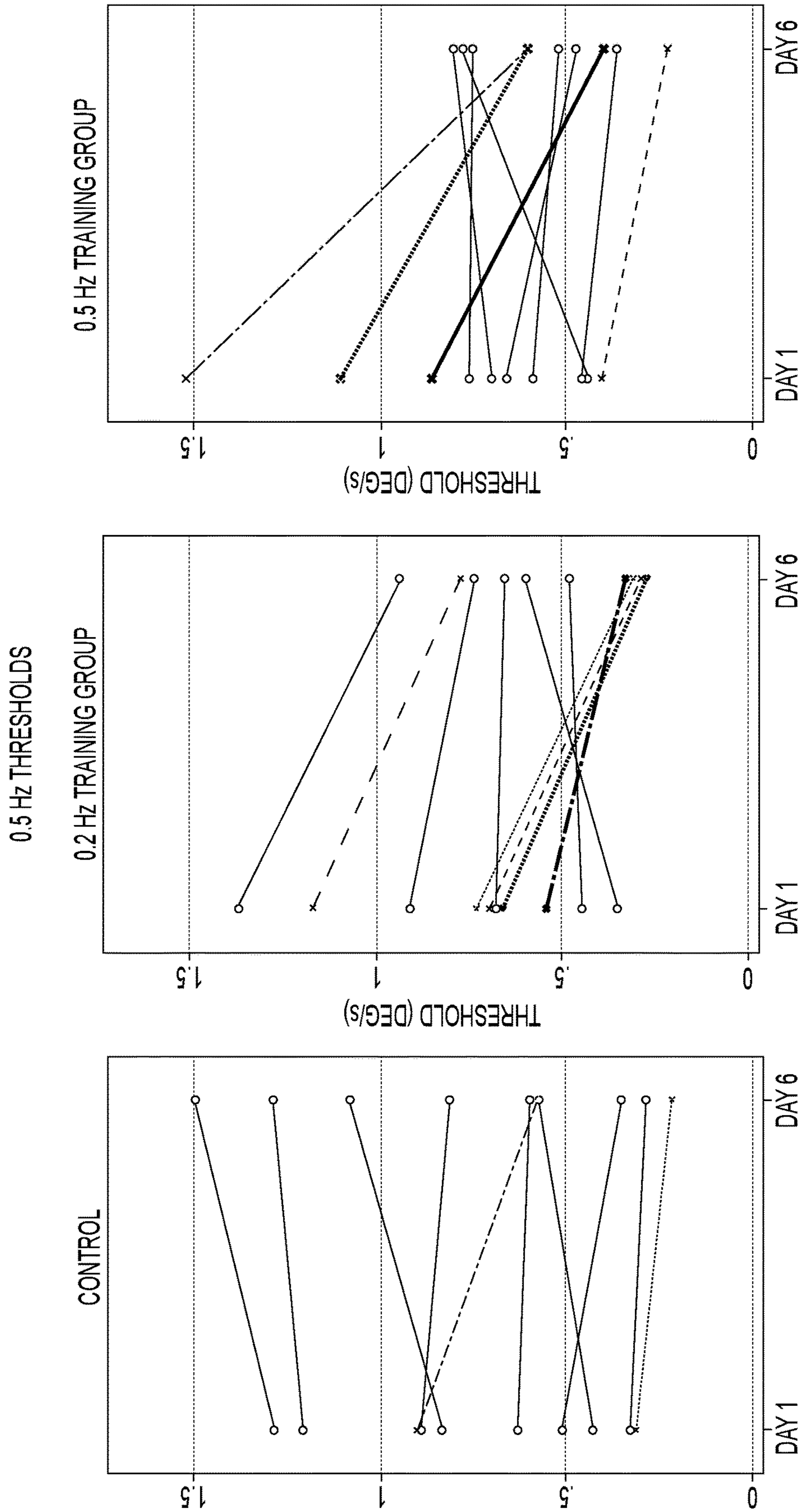
Figure 3C:
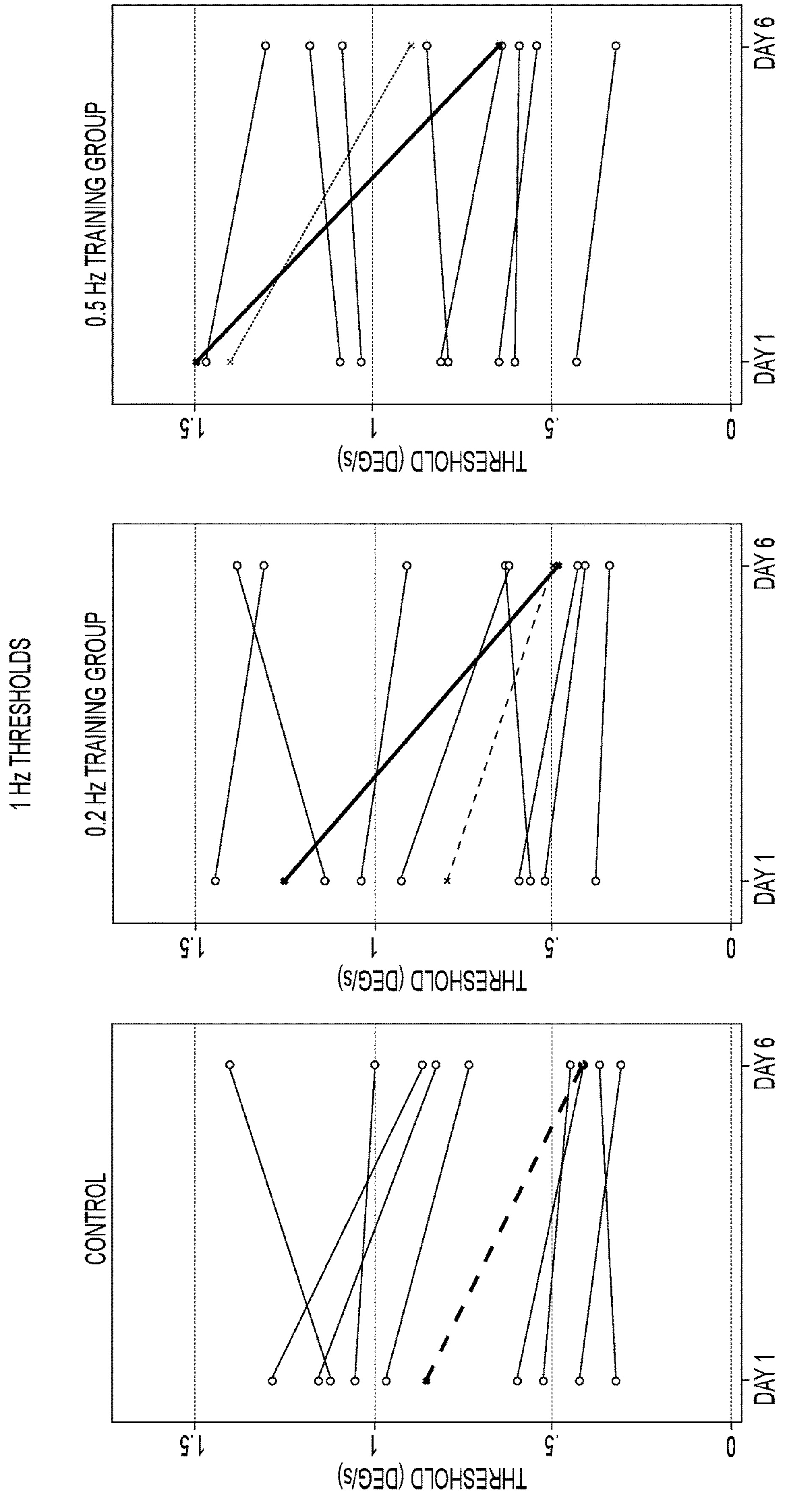

After visualizing the data, clusters of "responders" were observed within both the 0.5 and 0.2 Hz training groups, such that approximately half of the subjects appeared to experience a marked decrease in thresholds, while others show relatively stable performance (FIG. 3). To quantify this effect, subjects were categorized as "responders" based upon their percent change in thresholds, using a threshold of 32% as an indicator of a meaningful change. This is based upon prior data showing that thresholds, on average, are expected to vary on a within subject basis by one standard deviation or 16% (e.g., 0.16°/s for a threshold of 1°/s); thus, a cut-off at two standard deviations or 32% was set. For 0.2 Hz thresholds, 50% (5/10) of the 0.2 Hz training group and 30% (3/10) of the 0.5 Hz group were categorized as responders, compared to 0% (0/10) of the control group. Similarly, for 0.5 Hz thresholds, 50% (5/10) of the 0.2 Hz training group and 40% (4/10) of the 0.5 Hz group were categorized as responders, and only 10% (1/10) of the control subjects improved by at least 32% (N=1 with a 36.2% change). This behavior was not observed for 1 Hz roll tilt, where similar changes were seen between all three groups; 10% of the control group, 20% of the 0.2 Hz group, and 20% of the 0.5 Hz group improved by at least 32%.

Table 4 shows the age and baseline thresholds for the "responder" and "non-responder" groups, defined by those who showed an improvement of at least 2 SDs on either 0.2 or 0.5 Hz thresholds. Logistic regression was performed to determine the effect of age, sex, and baseline thresholds on responder status. No significant effects were observed (p>0.05) suggesting that the heterogeneity in treatment responses were due to individual differences in the response to the intervention or due to an unaccounted-for confounding variable (cognition, attention, motivation, etc.); the inclusion of healthy, asymptomatic young adults without a significant medical history favors the former, such that individuals may vary in their "optimal" training stimulus or dosage of training.

TABLE 4

Baseline characteristics of those who improved by at least 2 SD's on either the 0.2 Hz or 0.5 Hz condition (responders) compared to those who did not (non-responders) amongst those in the training groups (N = 20). A logistic regression model was used to determine the effect each characteristic on the odds of being a responder (significance at p <0.05).

| | Responders (N = 11) | Non-Responders (N = 9) | p-value |
|---|---|---|---|
| Age (years) | 23.45 (2.94) | 25.0 (3.87) | 0.54 |
| Sex (# females) | 8 (73%) | 3 (33%) | 0.12 |
| Baseline 0.2 Hz (°/s) | 0.59 (0.28) | 0.42 (0.09) | 0.18 |
| Baseline 0.5 Hz (°/s) | 0.88 (0.36) | 0.60 (0.19) | 0.34 |
| Baseline 1 Hz (°/s) | 0.95 (0.36) | 0.88 (0.38) | 0.33 |

Effect of Roll Tilt Adaptation on Balance

The original hypothesis was that the greatest change in balance performance would be observed in the "eyes closed, on foam" condition, where vestibular cues are thought to dominate. The 0.2 Hz group showed an average decrease in sway of 17.16% (p<0.001), and the 0.5 Hz group similarly improved by an average of 20.47% (p<0.001). However, unexpectedly, the control group also improved by a similar amount (15.16%; p<0.001) suggesting improvements were not specific to the training groups. The changes were significant for all three groups without a significant group by time interaction, suggesting that the effects of time were similar for each of the three groups (FIG. 4).

Figure 4:
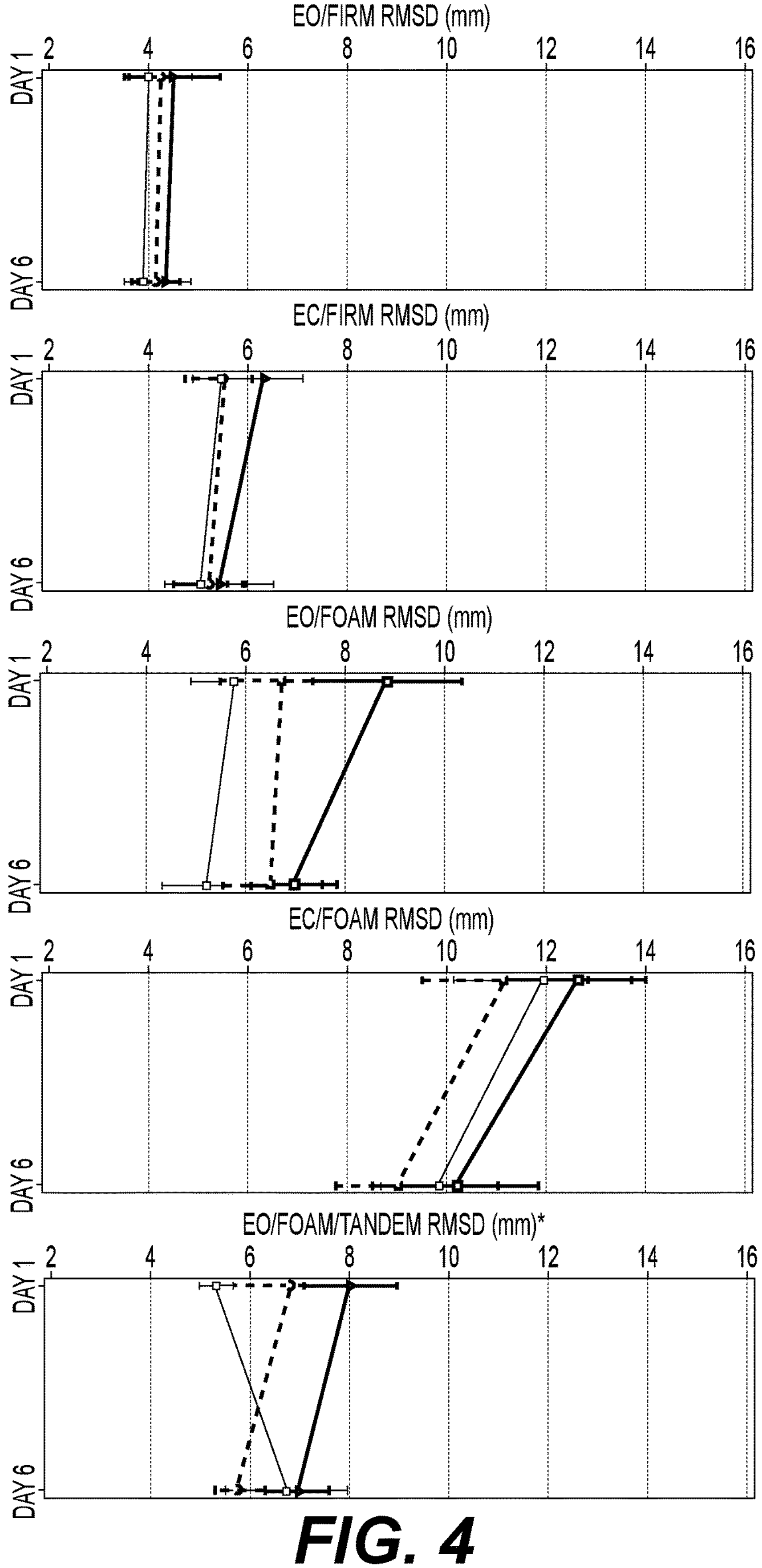
FIG. 4 illustrates mean root mean square distance (RMSD) of the mediolateral CoP for the control group (black), the 0.2 Hz training group (orange), and the 0.5 Hz training group (green) measured on Day 1 and Day 6. Error bars represent 1 SD. The "*" signifies that only 7/10 subjects in the 0.5 Hz group and 9/10 in the 0.2 Hz group were analyzed in the fifth condition due to falls. EO=eyes open, EC=eyes closed.
Figure 5A:
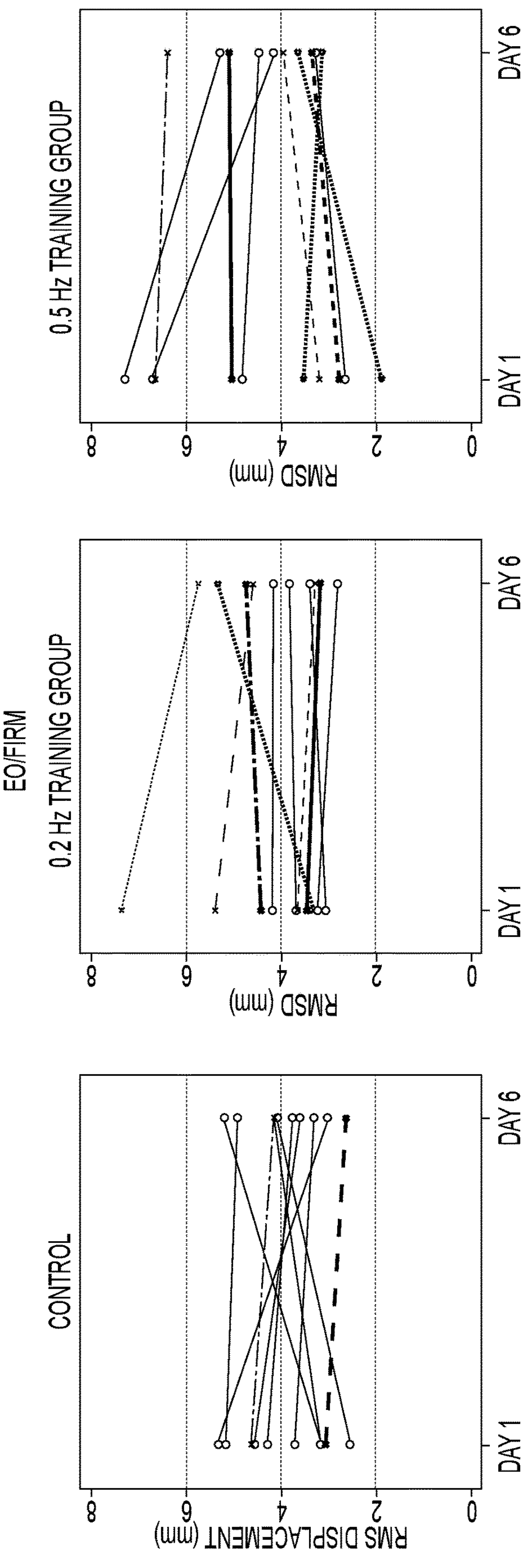
FIGS. 5A-5E illustrate root mean square distance (RMSD) of the medio-lateral CoP for each individual on Day 1 and Day 6 for the first five balance conditions. Participants who were labeled "responders" (i.e., demonstrating an improvement in threshold by at least 32%) for either of the actively trained thresholds (i.e., 0.2 or 0.5 Hz) are uniquely color coded in each panel; these unique color codes are also found for individual subjects in FIGS. 3A-3C. In panel E, an RMSD of zero indicates that the participant did not complete the trial. Condition 6 (eyes closed, foam surface tandem stance) is not included due to the limited number of participants (5 of 30) who could complete the condition. EO=eyes open, EC=eyes closed.
Figure 5B:
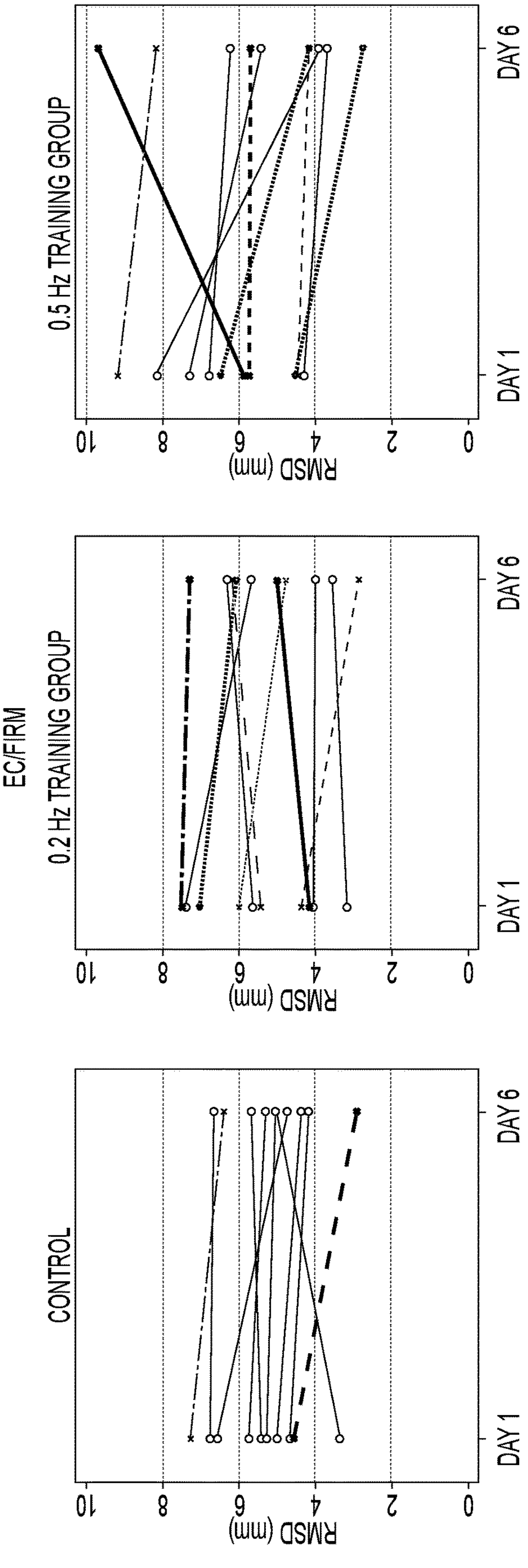
Figure 5C:
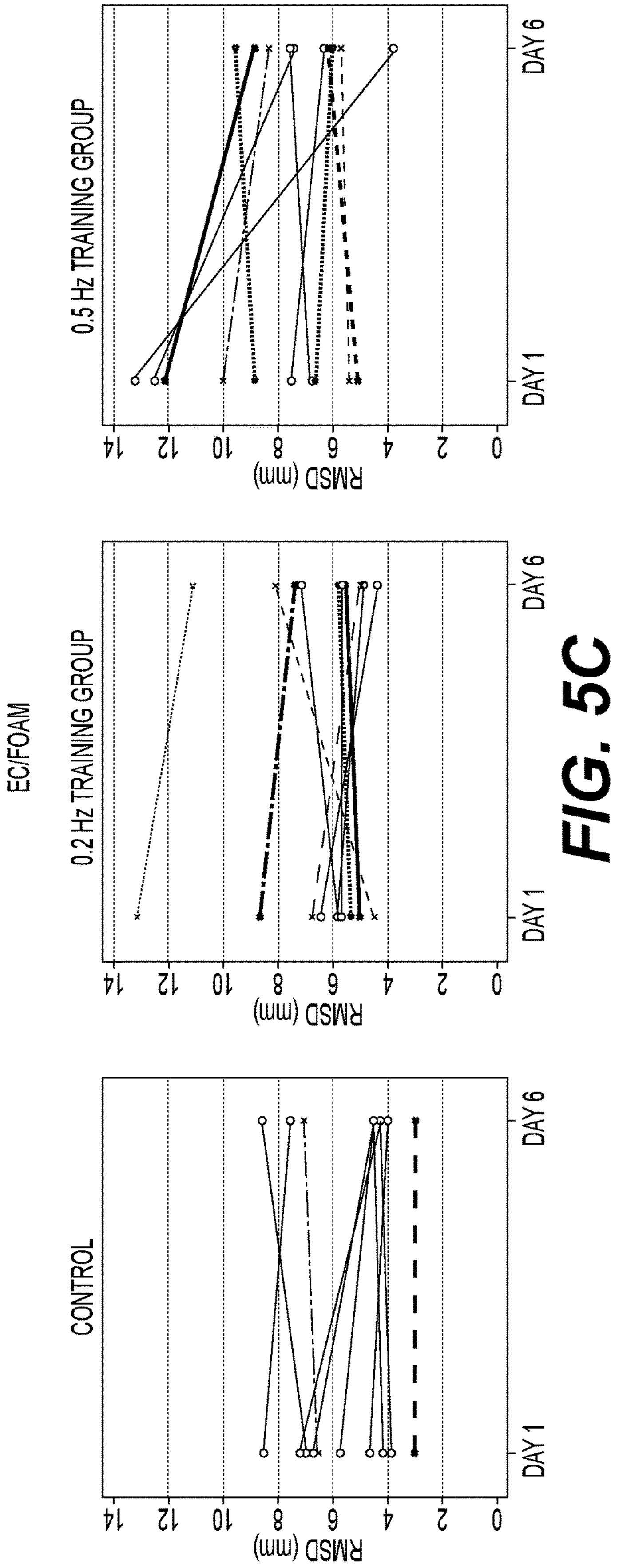
Figure 5D:
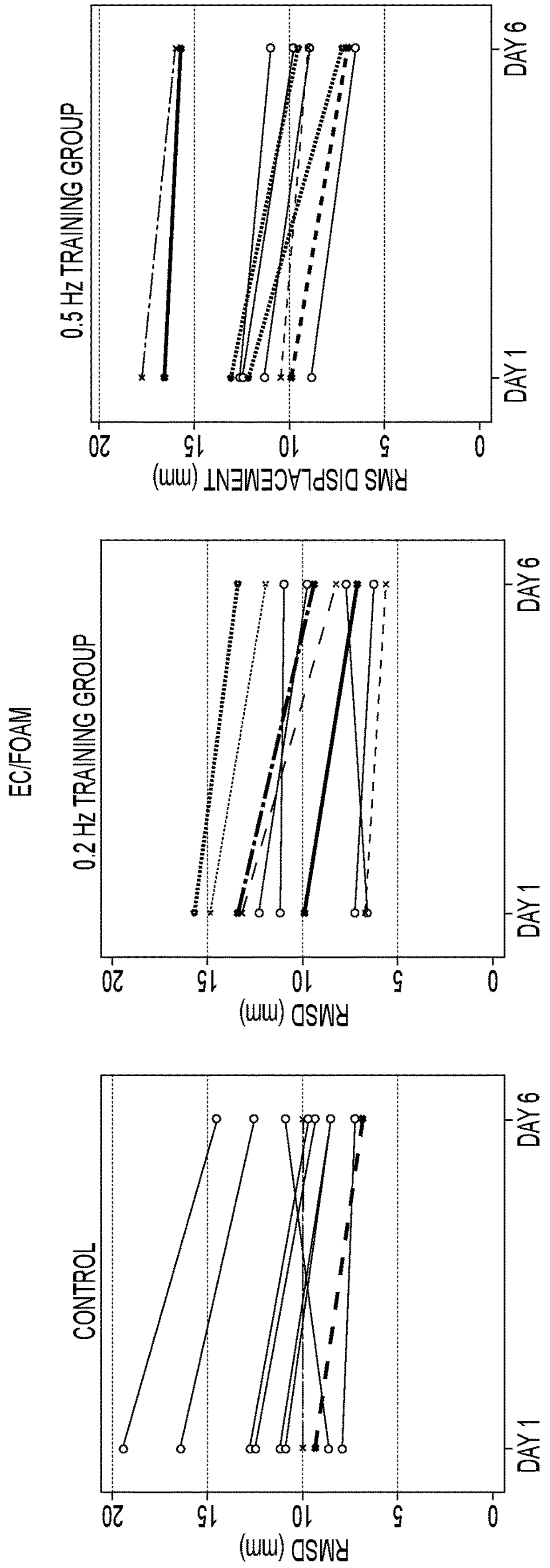
Figure 5E:
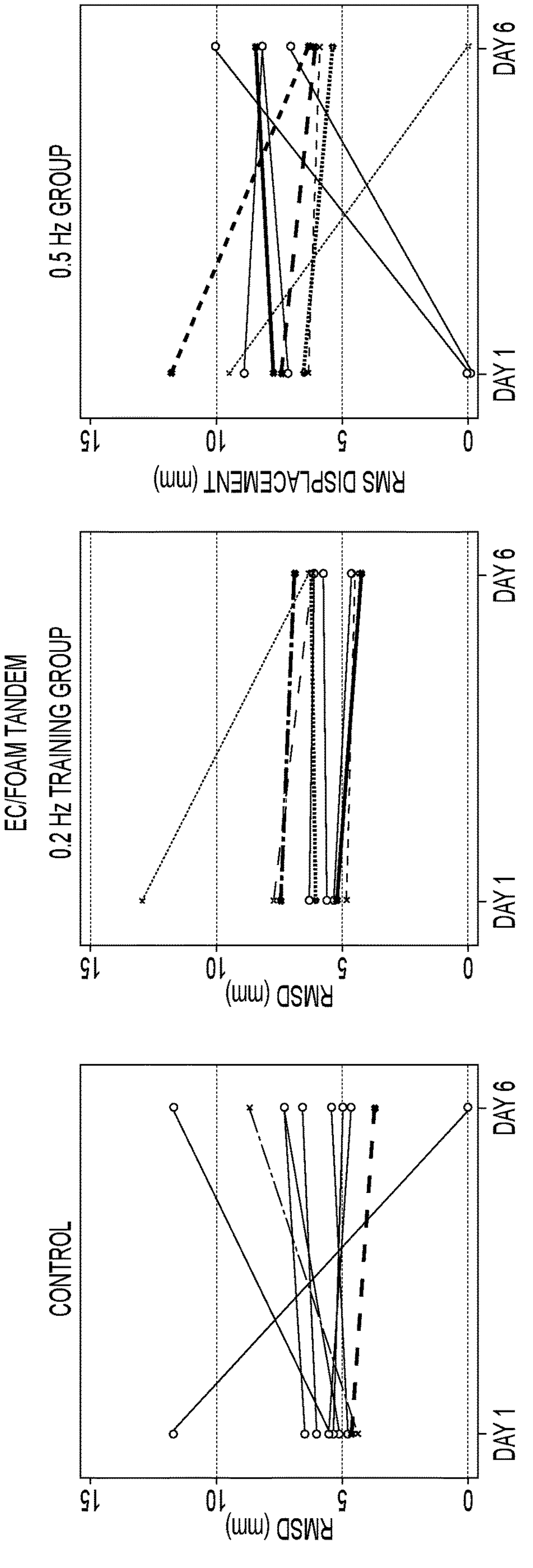

In the "eyes open, firm" and the "eyes closed, firm" conditions the RMSD was largely unchanged for both the training groups as well as the control group, with the exception of a non-significant reduction of 12.8% for the 0.5 Hz group in the EC/firm condition (Table 5, FIG. 4). In the remaining "eyes open, foam" condition, the 0.5 Hz group showed a significant reduction in sway (p=0.032), averaging a 13.8% decrease following the intervention. Finally, in the "eyes open, on foam in tandem" condition, both the 0.2 and 0.5 Hz groups improved by more than 10%, but the effects were not significant (Table 5, FIG. 4). Due to falls, only 7/10 subjects in the 0.5 Hz group and 9/10 in the 0.2 Hz group were analyzed in this fifth condition. Much like roll tilt thresholds, changes in balance performance varied between subjects (FIG. 5).

sway was less robust relative to the effects on vestibular perceptual thresholds, however, a significant reduction in postural sway was observed for the 0.5 Hz group in two of the conditions where proprioceptive cues were degraded (i.e., where vestibular cues are more important for postural stability).

Mechanism of Perceptual Adaptation

The stimulus for adaptation of the VOR is generally considered to be the induction of a "retinal slip" (i.e., movement of a visual image off of the fovea) error signal. The disparity between the visual target and fovea is thought to trigger central visuo-vestibular mechanisms that act to reduce the blurring of vision through the generation of preprogrammed eye movements and compensatory saccades, as well as a modest increase in slow phase eye velocity. In the perceptual adaptation paradigm described here, the training takes place in the dark, and thus, no such retinal slip error could have been provided. As a result, the mechanism underlying adaptation in the perceptual domain requires further study, but, given that the roll tilt training stimuli activate both the canals and otoliths, it is presumed that the underlying adaptation mechanism enhances canal-otolith integration.

TABLE 5

Average percent change (positive = increase, negative = decrease) in RMSD for each group in each of the 5 primary balance conditions. Corrected p-values are reported in parentheses and represents the results of the post-hoc test comparing RMSD between days 1 and 6 of the protocol.

| | EO/Firm | EC/Firm | EO/Foam | EC/Foam | EO/Foam/ Tandem |
|---|---|---|---|---|---|
| Control | +3.77 (1.0) | −5.93% (1.0) | −7.56 (1.0) | −15.16% (<0.001*) | +2.80 (0.696) |
| 0.2 Hz | +1.18 (1.0) | −3.47 (1.0) | +1.78 (1.0) | −17.16 (<0.001*) | −11.46 (0.483) |
| 0.5 Hz | +6.46 (1.0) | −12.83 (0.153) | −13.80 (0.032*) | −20.47 (<0.001*) | −10.16 (0.796) |

*= significant at a Bonferroni corrected alpha of 0.05.
EO = eyes open,
EC = eyes closed.

Given the young, healthy population of interest, a sixth balance condition was included to fully capture any subclinical balance deficits; subjects were asked to stand in tandem, on a foam pad with the eyes closed. Only 5/30 (16.7%) of the participants were able to stand for 30 seconds when given two attempts at the baseline assessment. At follow up, four of these five subjects again completed the balance task, showing an average decrease in ML RMSD of −14.9% (−28.8%, +18.5%, −12.9%, and −36.5% respectively). Interestingly, these four subjects were all in the 0.2 Hz training group and showed an average change of −22.24% in 0.2 Hz thresholds and −35.59% in 0.5 Hz thresholds. In addition, at the follow up assessment, four subjects (control=2, 0.5 Hz=1, 0.2 Hz=1) who failed this task at baseline were able to stand for at least 30 seconds; this cohort showed an average decrease in 0.2 Hz thresholds of 14.2% (−54.1% to +24.2%) and 5.13% in 0.5 Hz thresholds (−32.3% to +74.5%) with changes in thresholds varying widely.

Discussion

The data show that 0.2 and 0.5 Hz roll tilt perceptual thresholds can be improved significantly in less than 5 hours of training by using an adaptative roll tilt training stimulus. Additionally, these data show that the training response can be robust; 55% (11/20) of subjects in the training groups improved either 0.2 or 0.5 Hz roll tilt thresholds by at least 2 SDs (i.e., 32%) whereas the control group displayed stable thresholds between days 1 and 6 (1/10 improving by more than 32%). The effect of training on quiet stance postural In contrast to studies of VOR adaptation, subjects were provided trial by trial feedback on their responses, with the expectation that learning would occur based upon the provided feedback. As a result, incorrect responses yield an error signal related to the conflict between the perceived and actual motion stimulus. The benefit of similar feedback has been established for auditory and visual perceptual training. Although several theories exist to describe the mechanisms underlying the positive effect of feedback on perceptual training, the Augmented Hebbian Reweighting Model (AHRM) has a body of evidence that supports its validity. In general, Hebbian learning describes an experience dependent improvement in performance that occurs secondary to a strengthening of the relevant synaptic connections. The AHRM attributes perceptual learning to a reweighting of the appropriate sensory pathways, such that the strength of synaptic connections within the most efficient channels are strengthened, and the least efficient pathways go unused, and are therefore weakened.

While the provision of a mechanistic explanation for the observed effect is beyond the scope of this study, there are likely shared elements between self-motion perceptual learning in the visual and vestibular domains. Specifically, as vestibular thresholds quantify sensory noise, it is posited that perceptual adaptation may lower thresholds by reweighting the more reliable, or "less noisy", central vestibular pathways. The absence of frequency specific effects for roll tilt adaptation suggests also a possible shared mechanism yielding improvements in both 0.2 and 0.5 Hz thresholds, motions which both require canal-otolith integration. Modeling efforts, analogous to those utilized in the visual system, should be conducted to provide an explanation for the observed effects. Studies comparing learning in the vestibular motor (i.e., VOR) and perceptual domains are also needed to determine whether characteristics previously shown to induce greater adaptation of the VOR (i.e., retinal slip) can yield similar effects for roll tilt perceptual training.

Roll Tilt Perception and Balance

In a sample of healthy older adults, previous studies showed that 0.2 Hz roll tilt thresholds were a significant predictor of the ability to complete an "eyes closed, on foam" balance task, a categorical analog to the quantitative measure of sway reported here. A subsequent mediation analysis showed that 0.2 Hz roll tilt thresholds mediated 46% of age-related imbalance. Together, these findings suggested that vestibular noise, as quantified by roll tilt thresholds, may contribute to subclinical balance impairment. However, despite the large effect and notable sample size (N=99) of this dataset, correlation cannot prove causation, and thus the supposition of whether vestibular noise "causes" imbalance has yet to be tested.

The data disclosed herein provides evidence that increased vestibular noise may be a potential cause of subclinical balance impairment. This is supported by the finding that the 0.5 Hz roll tilt adaptation intervention led to a significant reduction in postural sway in the "eyes open, on foam" and "eyes closed, on foam" balance conditions. This is consistent with recent data showing that 0.5 Hz roll tilt thresholds display a significant positive correlation with postural sway in the "eyes closed, on foam" condition.

Figure 6:
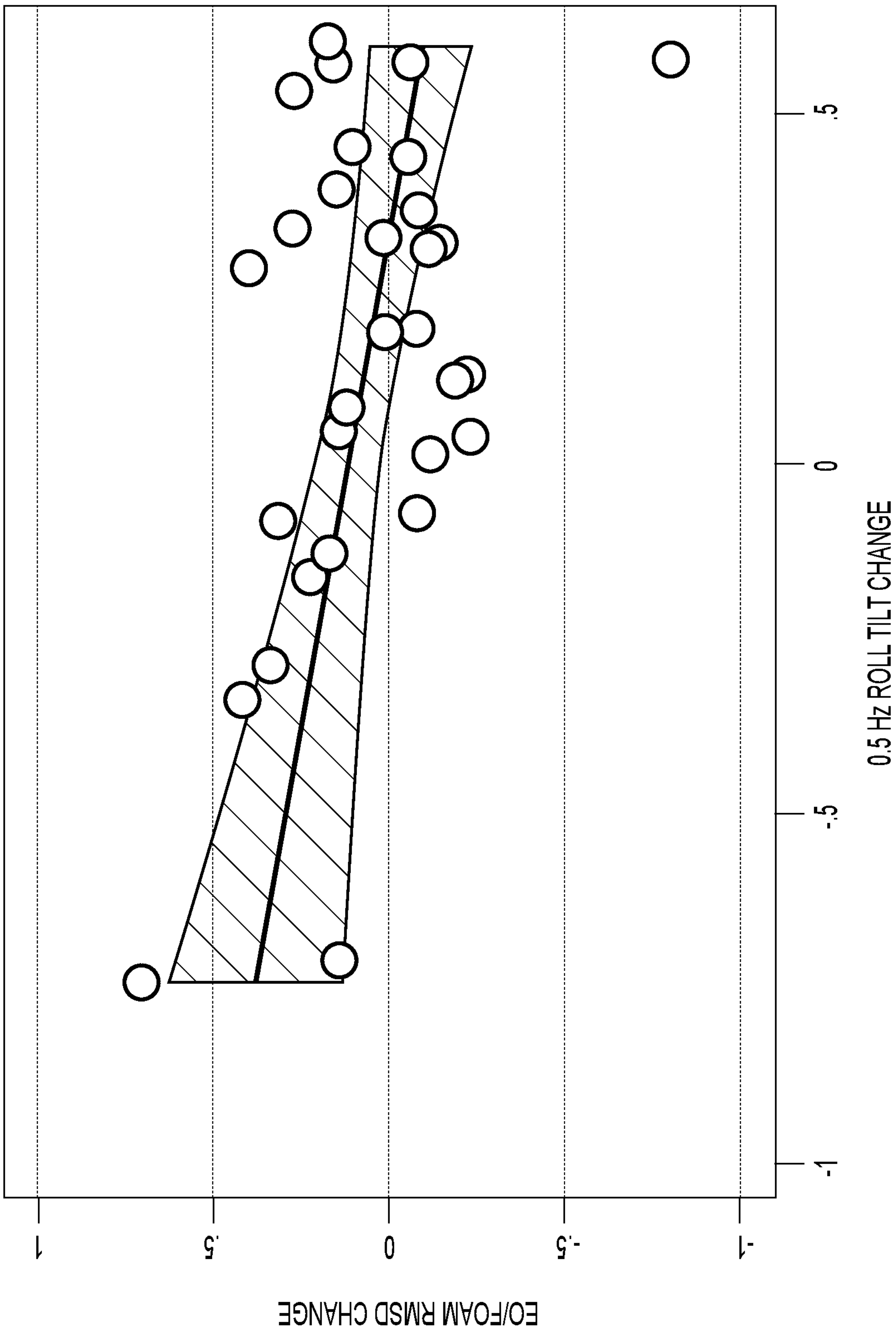
FIG. 6 illustrates percent change in the root mean square distance (RMSD) of the medio-lateral CoP for the two balance conditions (left=EO/Foam, right=EC/Foam) found to improve after 0.5 Hz roll tilt training is plotted against the percent change in 0.5 Hz roll tilt thresholds. Grey shading shows 95% confidence intervals.
Figure 6:
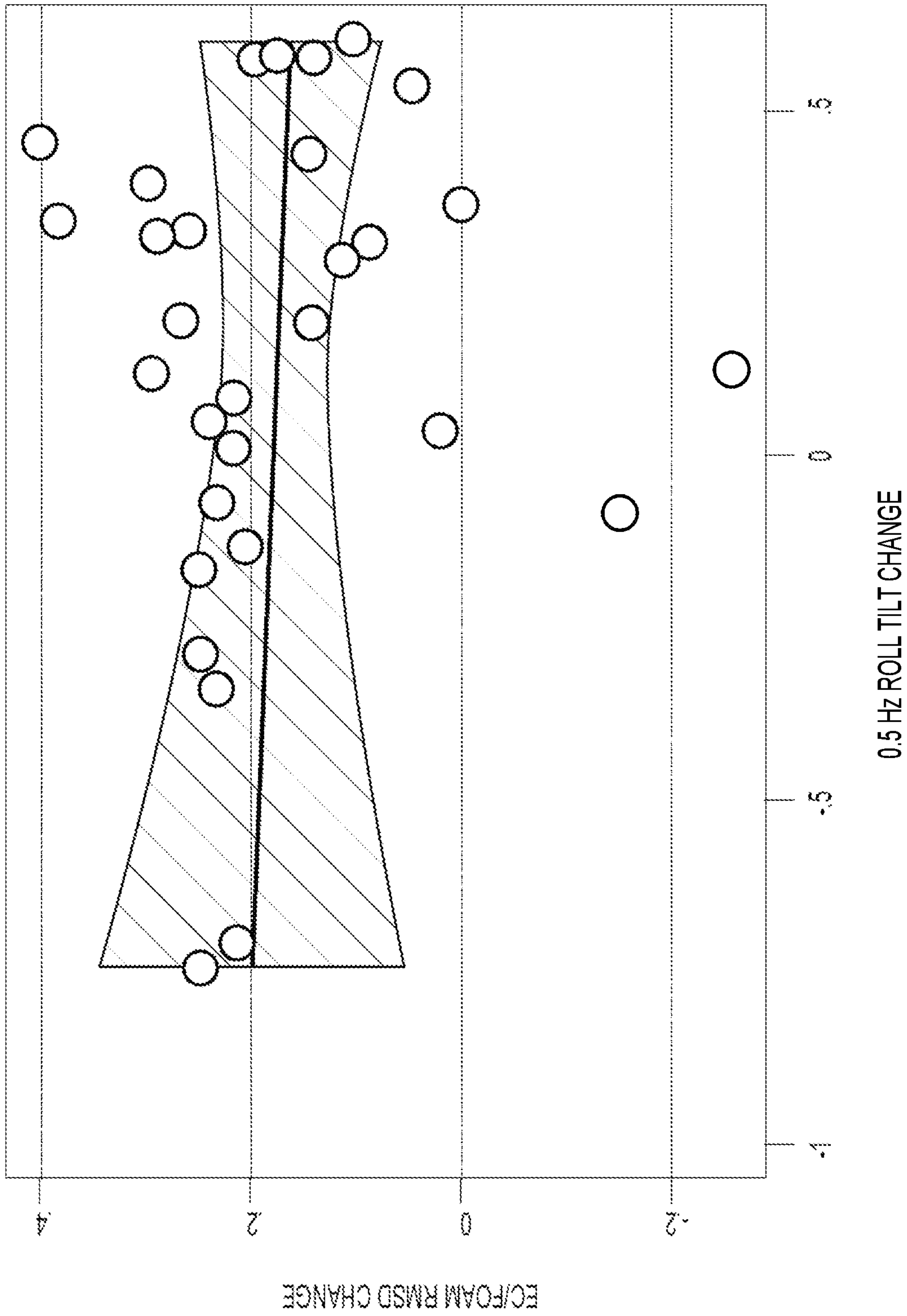

However, despite the reduction in sway, several findings temper the interpretation of this effect. First, the improvement for the 0.5 Hz group was variable, and the magnitude of change in thresholds did not display a significant positive correlation with the change in postural sway (FIG. 6; EO/Foam: $r=-0.28$, $p=0.140$, EC/Foam: $r=-0.13$, $p=0.483$). One explanation is that unintended factors (i.e., fatigue, motivation) could have preferentially impacted follow up threshold tests (due to the higher attentional demand), more so than balance assessments, in a subset of participants, yielding changes in balance but not thresholds. In addition, the control group also displayed a significant reduction in sway in the "eyes closed, on foam" condition, suggesting that a portion of the improvement in sway may be related to a learning effect, rather than the roll tilt intervention. The small effect sizes also likely result from the healthy population studied, where both balance and vestibular function were tightly distributed within a normal range. Additional studies should test the effect of roll tilt perceptual training on balance in older adults and/or patients with vestibular loss to determine the effect of improving perception in the presence of overt postural instability.

Comparison to Past Studies

Only one previous study attempted to improve roll tilt perception through a behavioral training paradigm. Previous studies showed that 1800 trials of roll tilt performed over the course of 9 days (9 hours total) led to an average improvement in 0.2 Hz roll tilt thresholds of 33%. The present disclosure shows that 0.2 Hz roll tilt thresholds can be improved with roughly 5 hours of training. The primary means by which training time was reduced was through the use of an adaptive training stimulus, which allowed for reduction of the number of training trials from 1800 to 1300. Additionally, the 0.5 Hz group received circa 3 hours of training as the 0.5 Hz stimulus lasts 2 seconds as compared to 5 seconds for 0.2 Hz. Because the specific dosage (time or repetitions) needed to induce perceptual learning are not fully known, the decreased exposure time for the 0.5 Hz group, compared to 0.2 Hz group, may explain the differences in learning observed. Similarly, the observed change in 0.2 Hz roll tilt thresholds of 23.8% for the 0.2 Hz training group was qualitatively less than was shown in previous studies (33%), suggesting that a higher time of exposure (9 vs. 5 hours) may be beneficial. Additional work is needed to determine the optimal dose of training, including whether the added time for training is worth the marginal difference in training outcomes.

In contrast to a previous study that reported that each of the 10 subjects in its training group showed an improvement in thresholds, a striking feature of the presently disclosed dataset was in the variability in responses to the training protocol. Factors that may explain the likelihood of showing a positive response to the intervention (i.e., a change of >32%) were investigated, but a significant difference in sex, age, or baseline thresholds between the responder and non-responder groups was not identified. One potential explanation is that the non-responders may have simply required additional repetitions compared to the responders. Future studies should determine the appropriate dosage (i.e., both time and repetitions) and whether an individualized intervention dose can be predicted to enable participants to reduce thresholds while avoiding overutilization of training resources.

Alternatively, it is possible that the proposed training intervention may not represent the "optimal" stimulus to induce perceptual learning; being that this is only the second such effort, this is certainly a feasible explanation. The 2D1U staircase, as was used here, targeted a challenging stimulus level where, on average, the subject should be able to perceive the direction of motion 70.7% of the time. Since simply guessing leads to an average accuracy of 50% (i.e., heads or tails judgement), the chosen stimuli were quite challenging and thus led to a sizeable proportion of errors. As a result, some subjects may have benefited from an easier task where they experienced a higher level of success. Individual preferences for success, as compared to challenge, may have also been one of the factors leading the clustering of responders and non-responders.

Finally, a body of literature supports that a visual error signal proves to be critical for inducing adaptation in the vestibulo-ocular reflex. Although the VOR and perceptual mechanisms have been shown to be qualitatively different, it remains possible that due to the shared central vestibular structures (i.e., vestibulo-cerebellum) that vestibular perceptual learning may benefit from a similar visual error signal (i.e., providing visual feedback on whether motion perception judgment is correct).

Implications for Rehabilitation

Existing methods for vestibular rehabilitation focus primarily on the recruitment of extra vestibular strategies to compensate for vestibular loss. In the case of vestibular lesions, these methods are robust and lead to marked improvements in dynamic visual acuity, reductions in dizziness, and improvements in postural control. However, in the presence of progressive sensorimotor changes (e.g., due to aging or neurodegenerative diseases) the availability of viable extra-vestibular sensory cues becomes limited, and thus, may constrain the effectiveness of rehabilitation. The present disclosure describes an intervention that aims to directly improve vestibular function by improving the signal to noise ratio of the self-motion roll tilt estimate, thereby avoiding the reliance on intact visual or proprioceptive cues.

In addition, perceptual symptoms of vestibular loss, namely vertigo and dizziness, have been shown to significantly impact quality of life, yet existing means to manage perceptual symptoms are limited. The repetitive exposure to provocative stimuli (i.e., habituation) is generally effective but requires tolerance of the intentional solicitation of symptoms over the course of weeks or months of training. Perceptual adaptation should be explored as a potential alternative to habituation training given its direct target of self-motion perception alongside a high level of tolerance.

Conclusion

Roll tilt perceptual adaptation led to improvements in perceptual thresholds for 0.2 and 0.5 Hz roll tilt whereas a control group showed stable thresholds. In approximately half of the subjects in the training groups, a robust improvement in roll tilt thresholds (>32% or 2 SDs) was observed, suggesting that variability exists in response to the training intervention. Among individuals who trained using a 0.5 Hz roll tilt stimulus, a reduction in postural sway in conditions where proprioceptive cues were degraded was observed, suggesting that increased vestibular noise may be a potential cause of increased postural sway in these conditions.

EXAMPLE

In further studies, a single asymptomatic older adult subject (female, 67 years of age) was recruited to complete the 0.5-Hz training protocol. Relative to the cohort of young adult participants (Table 1), this individual showed elevated 0 S-Hz roll tilt thresholds and increased postural sway in the "eyes closed, on foam" condition. At the post-test assessment, a 51.4% decrease in 0.5-Hz roll tilt thresholds (day 1: 1.4°/s, 95% CI 1.34-1.46; day 6: 0.68°/s, 95% CI 0.66-0.80) and a 31.9% reduction in RMSD during the "eyes closed, on foam" balance task (day 1: 16.1 mm; day 6: 11.0 mm) was observed for this older adult participant. Interestingly, at the post-test assessment, the 67-year-old subject's roll tilt threshold and postural sway were each lower than the mean 0.5-Hz roll tilt threshold (0.74°/s) and RMSD (11.89 mm) values reported at baseline for the young adult subjects with a mean age of 25 years old. Although only a single subject, these data support the prior supposition that changes with training may be greatest for those with elevated baseline postural sway and thresholds. In addition, when reassessed 8 weeks after the post-test assessment, the 67-year-old subject was found to have 0.5-Hz roll tilt thresholds (0.88°/s, 95% CI 0.85-0.90) and RMSD values (14.2 mm) that remained improved relative to her day 1 (pre-test) assessment. Future studies should test the effect of roll tilt perceptual training on balance in larger samples of older adults, as well as in individuals with vestibular loss, to determine the effect of roll tilt perceptual training on overt, rather than subclinical, postural instability.

Although specific embodiments of the disclosure have been described, one of ordinary skill in the art will recognize that numerous other modifications and alternative embodiments are within the scope of the disclosure. For example, while various illustrative implementations and structures have been described in accordance with embodiments of the disclosure, one of ordinary skill in the art will appreciate that numerous other modifications to the illustrative implementations and structures described herein are also within the scope of this disclosure.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments.

What is claimed is:

1. A vestibular training device for improving vestibular function and balance and reducing fall risk of a subject, the vestibular training device comprising:
- a motion platform configured to support the subject thereon and to execute a set of discrete motions;
- one or more input devices receiving input from the subject to provide responses to the motions executed by the motion platform;
- one or more feedback devices providing the subject with feedback indicative of whether the responses are correct or incorrect; and
- a controller in communication with the motion platform, the one or more input devices, and the one or more feedback devices, wherein the controller is configured to:
  - cause the motion platform to execute a first motion;
  - receive, via the one or more input devices, a first response indicative of the subject's perception of the first motion;
  - cause the one or more feedback devices to provide first feedback indicative of whether the first response is correct or incorrect;
  - determine a second motion based at least in part on the first response; and
  - cause the motion platform to execute the second motion;
  - receive, via the one or more input devices, a second response indicative of the subject's perception of the second motion;
  - cause the one or more feedback devices to provide second feedback indicative of whether the second response is correct or incorrect;
  - determine a threshold of the subject based at least in part on the first response and the second response, where the threshold is a biomarker for a fall risk of the subject; and
  - determine that the fall risk of the subject is acceptable when the threshold is below a predetermined percentile for young healthy adults.

2. The vestibular training device of claim 1, wherein the controller is further configured to:
- determine that training of the subject is recommended when the threshold is above the predetermined percentile.

3. The vestibular training device of claim 2, wherein the training is perceptual training, the perceptual training comprising tilt motions individually tailored to improve self-motion perception of the subject by lowering a tilt self-motion perceptual threshold of the subject.

4. The vestibular training device of claim 3, wherein the perceptual training comprises simultaneous and synchronous roll and pitch tilt motions individually tailored to lower a roll tilt perceptual threshold and a pitch tilt perceptual threshold of the subject.

5. The vestibular training device of claim 2, wherein the training is perceptual training, the perceptual training comprising motions individually tailored to improve self-motion perception of the subject by lowering a self-motion perceptual threshold of the subject.

6. The vestibular training device of claim 1, wherein the controller is further configured to:

determine a plurality of additional motions based at least in part on the second response; cause the motion platform to execute the additional motions;

receive, via the one or more input devices, a plurality of additional responses indicative of the subject's perception of the additional motions;

cause the one or more feedback devices to provide a plurality of additional feedback indicative of whether the additional responses are correct or incorrect; and determine the threshold of the subject based at least in part on the first response, the second response, and at least in part of the additional responses.

7. The vestibular training device of claim 6, wherein the controller is further configured to:

determine the threshold of the subject based at least in part on the first response and the second response, while excluding an outlier response deviating from the first response and the second response by a response threshold amount, wherein the outlier response is indicative of a lapse by the subject.

8. The vestibular training device of claim 1, wherein the discrete motions are individually tailored for the subject based at least in part on a previously determined threshold for the subject based at least in part on the first response and the second response.

9. The vestibular training device of claim 8, wherein the discrete motions are individually tailored for the subject to be at the previously determined threshold for the subject.

10. The vestibular training device of claim 1, wherein the controller is further configured to:

receive, via the one or more input devices, a second response indicative of the subject's perception of the second motion;

cause the one or more feedback devices to provide second feedback indicative of whether the second response is correct or incorrect;

determine a third motion based at least in part on the second response; and cause the motion platform to execute the third motion.

11. The vestibular training device of claim 1, wherein the controller is further configured to compare the fall risk of the subject to values from a previously quantified population.

12. The vestibular training device of claim 1, wherein the discrete motions are incrementally changed over the course of a training session.

13. The vestibular training device of claim 1, wherein the one or more input devices comprise one or more handheld devices configured to enable the subject to provide the responses to the motions executed by the motion platform.

14. The vestibular training device of claim 1, wherein the one or more feedback devices includes an auditory feedback device and/or a visual feedback device providing the subject with a corresponding auditory and/or visual feedback indicative of whether the responses are correct or incorrect.

15. The vestibular training device of claim 1, further comprising noise-cancelling headphones configured to emit white noise while the motion platform executes each of the discrete motions, and a visual display configured to present visual information during testing or training.

16. The vestibular training device of claim 1, further comprising a visual display configured to present visual information during testing or training.

17. A method for improving vestibular function and balance and reducing fall risk of a subject using a vestibular training device comprising a motion platform configured to support the subject thereon and to execute a set of discrete motions, one or more input devices configured to enable the subject to provide responses to the motions executed by the motion platform, one or more auditory and/or visual feedback devices providing the subject with a corresponding auditory and/or visual feedback indicative of whether the responses are correct or incorrect, and a controller in communication with the motion platform, the one or more input devices, and the one or more feedback devices, the method comprising:

causing the motion platform to execute a first motion;

receiving, via the one or more input devices, a first response indicative of the subject's perception of the first motion;

causing the one or more feedback devices to provide first feedback indicative of whether the first response is correct or incorrect;

determining a second motion based at least in part on the first response;

causing the motion platform to execute the second motion;

receiving, via the one or more input devices, a second response indicative of the subject's perception of the second motion;

cause the one or more feedback devices to provide second feedback indicative of whether the second response is correct or incorrect;

determining a threshold of the subject based at least in part on the first response and the second response, where the threshold is a biomarker for a fall risk of the subject; and determining that the fall risk of the subject is acceptable when the threshold is below a predetermined percentile for young healthy adults.

18. The method of claim 17, further comprising:

determining a third motion based at least in part on the second response; and causing the motion platform to execute the third motion.

19. The method of claim 17, further comprising:

determining a plurality of additional motions based at least in part on the second response;

causing the motion platform to execute the additional motions;

receiving, via the one or more input devices, a plurality of additional responses indicative of the subject's perception of the additional motions;

causing the one or more feedback devices to provide a plurality of additional feedback indicative of whether the additional responses are correct or incorrect; and determining a threshold of the subject based at least in part on the first response, the second response, and at least in part of the additional responses, wherein the threshold is a biomarker for a fall risk of the subject.

20. The method of claim 19, further comprising:

determining the threshold of the subject based at least in part on the first response and the second response, while excluding an outlier response deviating from the first response and the second response by a response threshold amount, wherein the outlier response is indicative of a lapse by the subject.

* * * * *